US007186817B2

(12) United States Patent  
Rasmussen et al.

(10) Patent No.: US 7,186,817 B2
(45) Date of Patent: Mar. 6, 2007

(54) POLYNUCLEOTIDES ENCODING PHYTASE POLYPEPTIDES

(75) Inventors: Søren Rasmussen, Roskilde (DK); Mikael Blom Sørensen, Copenhagen (DK); Katja Salomon Johansen, Gentofte (DK)

(73) Assignee: Forskningscenter Risø, Roskilde (DK)

( * ) Notice: Subject to any disclaimer, the term of this patent is extended or adjusted under 35 U.S.C. 154(b) by 145 days.

(21) Appl. No.: 10/275,311

(22) PCT Filed: May 4, 2001

(86) PCT No.: PCT/DK01/00314

§ 371 (c)(1), (2), (4) Date: May 5, 2003

(87) PCT Pub. No.: WO01/83763

PCT Pub. Date: Nov. 8, 2001

(65) Prior Publication Data

US 2004/0086997 A1 May 6, 2004

(30) Foreign Application Priority Data

May 4, 2000 (DK) ............... 2000 00741

(51) Int. Cl.
C07H 21/04 (2006.01)
C12P 21/00 (2006.01)
C12N 9/10 (2006.01)
C12N 1/20 (2006.01)
C12N 15/63 (2006.01)

(52) U.S. Cl. .................. 536/23.2; 435/70.1; 435/71.1; 435/196; 435/252.3; 435/320.1

(58) Field of Classification Search ................. 435/196
See application file for complete search history.

(56) References Cited

FOREIGN PATENT DOCUMENTS

| WO | WO 91/14782 A | 10/1991 |
| WO | WO 98/20139 A | 5/1998 |
| WO | WO 99/48380 A | 9/1999 |

OTHER PUBLICATIONS

Witkowski et al, Conversion of a beta-ketoacyl synthase to a malonyl decarboxylase by replacement of the active-site cysteine with glutamine. Biochemistry. Sep. 7, 1999;38(36):11643-11650.*
Wishart et al, A single mutation converts a novel phosphotyrosine binding domain into a dual-specificity phosphatase. J Biol Chem. Nov. 10, 1995;270(45):26782-26785.*
Mitchell et al., The phytase subfamily of histidine acid phosphatases: isolation of genes for two novel phytases from the fungi *Aspergillus terreus* and *Myceliophthora thermophila*. Microbiology. Jan. 1997;143 ( Pt 1):245-52.*
Maugenest et al., Cloning and characterization of a cDNA encoding a maize seedling phytase. Biochem J. Mar. 1, 1997;322 ( Pt 2):511-7.*
A_GeneSeq database Accession No. ABB09601 May 29, 2002 Grabau et al. Alignment with Seq ID No. 8.*
Hegeman et al, A novel phytase with sequence similarity to purple acid phosphatases is expressed in cotyledons of germinating soybean seedlings. Plant Physiol. Aug. 2001;126(4):1598-608.*
SIGMA Catalogue, *Molecular Biology*, 1998, Product P 1259, Phytase from wheat, XP002154966, p. 900.
Murray, E.E., et al., "Condon Usage in Plant Genes," *Nucleic Acids Research* 17(2):477-498, Jan. 25, 1989.
Nakamura, Y., et al., "Condon Usage Tabulated From International DNA Sequence Databases: Status for the Year 2000," *Nucleic Acids Research* 28(1):292, 2000.
Akama, K., et al., "Efficient Transformation of *Arabidopsis thaliana*: Comparison of the Efficiencies With Various Organs, Plant Ecotypes and Agrobacterium Strains," *Plant Cell Reports* 12:7-11, 1992.
Baldi, B.G., et al., "Localization of Constitutive Phytases in Lily Pollen and Properties of the pH 8 Form," *Plant Science* 56:137-147, 1988.
Barrientos, L., et al., "Specificity of Hydrolysis of Phytic Acid by Alkaline Phytase From Lily Pollen," *Plant Physiol.* 106:1489-1495, 1994.
Bateman, A., et al., "Pfam 3.1: 1313 Multiple Alignments and Profile HMMs Match the Majority of Proteins," *Nucleic Acids Research* 27(1):260-262, 1999.
Christou, P., "Genetic Transformation of Crop Plants Using Microprojectile Bombardment," *The Plant Journal* 2(3):275-281, 1992.
Crossway, A., "Integration of Foreign DNA Following Microinjection of Tobacco Mesophyll Protoplasts," *Mol. Gen. Genet.* 202:179-185, 1986.
Deblaere, R., et al., Efficient Octopine Ti Plasmid-Derived Vectors for *Agrobacterium*-Mediated Gene Transfer to Plants, *Nucleic Acids Research* 13(13):4777-4788, 1985.

(Continued)

Primary Examiner—Sheridan Swope
(74) Attorney, Agent, or Firm—Christensen O'Connor Johnson Kindness PLLC

(57) ABSTRACT

The present invention relates to isolated polypeptides having phytase activity, recombinant DNA sequences encoding such polypeptides, methods of producing such polypeptides, and the use of the polypeptides in transgenic plants. The invention discloses polypeptides having affinity for the substrate phytate (1, 2, 3, 4, 5, 6 myo-inositol-hexakisphosphate, phytic acid), comprising an amino acid sequence as described by the invention. Furthermore, the invention discloses DNA fragments encoding the polypeptides, and cDNA fragments encoding the polypeptides. The polypeptides of the invention may, for example, be used as an additive in animal feeds, an additive in food for human consumption, or to extract proteins from rice bran. The invention also concerns a transgenic plant or part thereof, wherein the plant or part thereof has been genetically modified to comprise a polypeptide as defined by the invention.

6 Claims, 9 Drawing Sheets

OTHER PUBLICATIONS

Dvorakova, J., "Phytase: Sources, Preparation and Exploitation," *Folia Microbiol.* 43(4):323-338 (1998).

Edwards, J.W., and G.M. Coruzzi, "Cell-Specific Gene Expression in Plants," *Annu. Rev. Genet.* 24:275-303, 1990.

Ehrlich, K.C., et al., "Identification and Cloning of a Second Phytase Gene (phyB) From *Aspergillus niger (ficuum)*," *Biochemical and Biophysical Research and Communications* 195(1):53-57, 1993.

Eeckhout, W., and M. De Paepe, "Total Phosphorus, Phytate-Phosphorus and Phytase Activity in Plant Feedstuffs," *Animal Feed Science and Technology* 47:19-29, 1994.

Engelen, A.J., et al., "Simple and Rapid Determination of Phytase Activity," *Journal of AOAC International* 77(3):760-764, 1994.

Franck, A., et al., "Nucleotide Sequence of Cauliflower Mosaic Virus DNA," *Cell* 21:285-294, 1980.

Gasser, C.S., and R.T. Fraley, "Genetically Engineering Plants for Crop Improvement," *Science* 244:1293-1299, 1989.

Gibson, D.M., and A.H.J. Ullah, "Purification and Characterization of Phytase from Cotyledons of Germinating Soybean Seeds," *Archives of Biochemistry and Biophysics* 260(2):503-513, 1988.

Gibson, D.M., and A.B.J. Ullah, *Inositol Metabolism in Plants*, Wiley-Liss, Inc., New York, 1990, Chap. 6, "Phytases and Their Action on Phytic Acid," pp. 77-92.

Gram, N.H., "The Ultrastructure of Germinating Barley Seeds. I. Changes in the Scutellum and the Aleurone Layer in Nordal Barley," *Carlsberg Res. Commun.* 47:143-162, 1982.

Hoffmann, K., et al., "The PROSITE Data, its Status in 1999," *Nucleic Acids Research*, 27(1):215-219, 1999.

Hooykaas, P.J.J., and R.A. Schilperoot, "Agrobacterium and Plant Genetic Engineering," *Plant Molecular Biolog.* 19:15-38, 1992.

Irving, G.C.J., *In Inositol Phosphates: Their Chemistry, Biochemistry and Physiology*, Elsevier Scientific Publishing Company, Amsterdam, 1980, Chap. 11, "Intermediates in the Dephosphorylation of $P_6$-Inositols by Phytase Enzymes", pp. 99-117.

Ito, M., et al., "Meristem-Specific Gene Expression Directed by the Promoter of the S-Phase-Specific Gene, *cyc07*, in Transgenic *Arabidopsis*," *Plant Molecular Biolog.* 24:863-878, 1994.

Jia, Z., et al., "Purification, Crystallization and Preliminary X-ray Analysis of the *Escherichia coli* Phytase," *Acta Cryst.* D54:647-649, 1998.

Joshi, R.L., and V. Joshi, "Strategies for Expression of Foreign Genes in Plants. Potential Use of Engineered Viruses," *FEBS Letters* 281(1,2):1-8, 1991.

Kerovuo, J., et al., "Isolation, Characterization, Molecular Gene Cloning, and Sequencing of a Novel Phytase from *Bacillus subtilis*," *Applied and Environmental Microbiology* 64(6):2079-2085, 1998.

Kerovuo, J. et al., "Analysis of *myo*-inositol hexakisphosphate hydrolysis by *Bacillus* phytase: indication of a novel reaction mechanism," Biochem. J. 352:623-628, 2000.

Kim, Y.-O., et al., Cloning of the thermostable phytase gene (*phy*) from *Bacillus* sp. DS11 and its overexpression in *Escherichia coli*, *FEMS Microbiology Letters* 162:185-191, 1998.

Klee, H. et al., *Agrobacterium*-Mediated Plant Transformation and its Further Applications to Plant Biology, *Ann. Rev. Plant Physiol.* 38:467-486, 1987.

Kyhse-Anderesen, J., "Electroblotting of multiple gels: a simple apparatus without buffer tank for rapid transfer of proteins from Polyacrylamide to nitrocellulose," *Journal of Biochemical and Biophysical Methods* 10:203-209, 1984.

Laboure, A., et al., "Purification and characterization of a phytase (*myo*-inositol-hexakisphosphate phosphohydrolase) accumulated in maize (*Zea mays*) seedlings during germination," *Biochem. J.* 295:413-419, 1993.

Larsson, O., et al., "Inhibition of Phosphatases and Increased $Ca^{2+}$Channel Activity by Inositol Hexakisphosphate," *Science* 278:471-474, 1997.

Lee, W.J., "Phytic Acid Content and Phytase Activity of Barley Malt," *ASBC Journal*, 1989, pp. 62-65.

Lim, P.E., and M.E. Tate, "The Phytases I. Lysolecithin-Activated Phytase From Wheat Bran," *Biochem. Biophys. Acta* 250:155-164, 1971.

Lim, P.E., and M.E. Tate, "The Phytases II. Properties of Phytase Fractions $F_1$ and $F_2$ from Wheat Bran and the *myo*-Inositol Phosphates Produced by Fraction $F_2$," *Biochimica et Biophysica Acta* 302:316-328 (1973).

Loewus, F., et al., "*myo*-Inositol metabolism in plants," *Plant Science* 150:1-19, 2000.

Maugenest, S. et al., "Structure of two maize phytase genes and their spatio-temporal expression during seedling development," *Plant Molecular Biology* 39:503-514, 1999.

Mitchell, D.B., et al., "The phytase subfamily of histidine acid phosphatases: isolation of genes for two novel phytases from the fungi *Aspergillus terreus* and *Myceliophthora thermophila*,"*Microbiology* 143:245-252, 1997.

Muir, S.R. and D. Sanders, "Inositol 1,4,5-Trisphosphate-Sensitive $Ca^{2+}$Release Across Nonvacuolar Membranes in Cauliflower," *Plant Physiol.* 114:1511-1521, 1997.

Munnik, T., et al., "Phospholipid signalling in plants," *Biochimica et Biophysica Acta* 1389:222-272, 1998.

Nagai, Y. and S. Funahashi, "Phytase (myoinositolhexaphosphate phosphohydrolase) from Wheat Bran. Part I. Purification and Substrate Specificity," *Agr. Biol. Chem.* 26(12), 794-803, 1962.

Nagai, Y. and S. Funahashi, "Phytase from Wheat Bran. Part II. Successive Dephosphorylation of *myo*-Inositol Hexaphosphate by Wheat Bran Phytase," *Agr. Biol. Chem.* 27(9):619-624, 1963.

Nakano, T., et al. "Purification and Characterization of Phytase Isozymes from Wheat Bran," *Niigata Daigaku Nogakubu Hokoku* 49(2):119-128, 1997.

Nakano, T., et al., "Purification and Characterization of Phytase from Bran of *Triticum aestivum* L. cv. Nourin #61," *Food Sci. Technol. Res.* 5(1):18-23, 1999.

Nielsen, H., et al., "Identification of prokaryotic and eukaryotic signal peptides and prediction of their cleavage sites," *Protein Engineering* 10(1):1-6, 1997.

Nishino, H., et al., Suppression of Lung and Liver Carcinogenesis in Mice by Oral Administration of *Myo*-inositol, *Anticancer Research* 19:3663-3664 (1999).

Pasamontes, L., et al., "Gene Cloning, Purification, and Characterization of a Heat-Stable Phytase from the Fungus *Aspergillus fumigatus*," *Applied and Environmental Microbiology* 63(5):1696-1700, 1997.

Pietrzak, M., et al., "Expression in plants of two bacterial antibiotic resistance genes after protoplast transformation with a new plant expression vector," *Nucleic Acids Research* 14(14):5857-5868, 1986.

Piddington, C.S., et al., "The cloning and sequencing of the genes encoding phytase (*phy*) and pH 2.5-optimum acid phosphatase (*aph*) from *Aspergillus niger* var. *awamori*," *Gene* 133:55-62, 1993.

Potrykus, I., "Gene Transfer to Cereals: An Assessment," *Biotechnology*, pp. 535-542, Jun. 1990.

Potrykus, I., "Gene Transfer to Plants: Assessment of Published Approaches and Results," *Annu. Rev. Plant Physiol. Plant Mol. Biol.* 42:205-225, 1991.

Rasmussen, S.K., and F. Hatzack, "Identification of two low-phytate barley (*Hordeum vulgare* L.) grain mutants by TLC and genetic analysis," *Hereditas* 129:107-112, 1998.

Scott, J.J., and F.A. Loewus, "A Calcium-Activated Phytase from Pollen of *Lilium longiflorum*," *Plant Physiol.* 82:333-335, 1986.

Shamsuddin, A.B., and I. Vucenik, "Mammary Tumor Inhibition by $IP_6$: A Review," *Anticancer Research* 19:3671-3674, 1999.

Sharp, P.J., et al., "Location of β-amylase sequences in wheat and its relatives," *Theoretical and Applied Genetics* 75:286-290, 1988.

Shimamoto, K., et al., "Fertile transgenic rice plants regenerated from transformed protoplasts," *Nature* 338:274-276, Mar. 1989.

Stitt, M., "Regulation of Metabolism in Transgenic Plants," *Annu. Rev. Plant Physiol. Plant Mol. Biol.* 46:341-368, 1995.

Tague, B.W., and M.J. Chrispeels, "Identification of a Plant Vacuolar Protein Targeting Signal in Yeast," *Plant Phys.* 86:Abst. 506, 1988.

Ullah, A.H.J., and H.C. Dischinger, Jr., "*Aspergillus ficuum* Phytase: Complete Primary Structure Elucidation by Chemical Sequencing," *Biochemical and Biophysical Research Communication* 192(2):747-753, 1993.

Ullah, A.H.J., and D.M. Gibson, "Extracellular Phytase (E.C. 3.1.3.8) from *Aspergillus ficuum* NRRL 3135: Purification and Characterization," *Preparative Biochemistry* 17(1):63-91, 1987.

Ullah, A.H.J., and K. Sethumadhavan, "Differences in the Active Site Environment of *Aspergillus ficuum* Phytase," *Biochemical and Biophysical Research Communications* 243:458-462, 1998.

Ullah, A.H.J., et al., "Characterization of Recombinant Fungal Phytase (*phyA*) Expressed in Tobacco Leaves," *Biochemical and Biophysical Research Communications* 264:201-206, 1999.

van Hartingsveld, W., et al., "Cloning, characterization and overexpression of the phytase-encoding gene (*phyA*) of *Aspergillus niger*," *Gene* 127:87-94, 1993.

York, J.D., et al., "A Phospholipase C-Dependent Inositol Polyphosphate Kinase Pathway Required for Efficient Messenger RNA Export," *Science* 285:96-100, 1999.

Yoshida, T., et al., "Phytase Activity Associated With Isolated Aleurone Particles of Rice Grains," *Agr. Biol. Chem.* 39(1):289-290, 1975.

Zhang, Z.-Y., et al., The Cys(X)$_5$Arg Catalytic Motif in Phosphoester Hydrolysis, *Biochemistry* 33:15266-15270, 1994.

Zupan, J.R. and P. Zambryski, "Transfer of T-DNA from *Agrobacterium* to the Plant Cell," *Plant Physiol.* 107:1041-1047, 1995.

Greiner, R., et al., Identification and Properties of myo-Inositol Hexakisphosphate Phosphohydrolases (Phytases) from Barley (*Hordeum vulgare*), *Journal of Cereal Science* 31:127-139, 2000.

Hatzack, F., et al., "Low Phytic Acid Mutants and High Phytase Crops: Two Strategies to Improve the Availability of Phosphate," *Plant Nutrition-Molecular Biology and Genetics*, pp. 121-124, 1999.

Khare, S. K., et al., "Entrapment of wheat phytase in polyacrylamide gel and its application in soymilk phytate hydrolysis," *Biotechnol. Appl. Biochem.* 19:193-198, 1994.

Nakano, T., et al., "The Pathway of Dephosphorylation of *myo*-Inositol Hexakisphosphate by Phytases from Wheat Bran of *Triticum aestivum* L. cv. Nourin #61," Biosci. Biotechnol. Biochem. 64(5):995-1003, 2000.

Niazi, A.H.K., et al., "Reduction of phytic acid content in rice bran meal," Chemical Abstracts 128(6):Abst. 320850x, Jun. 29, 1998.

"Putative Purple Acid Phosphatase" [online] EMBL Database, Accession No. Q9SFU3, May 1, 2000.

* cited by examiner

Fig. 8A.

|  | | 10 | 20 | 30 | 40 | 50 |
|---|---|---|---|---|---|---|
| Kidney bean | SEQ. ID NO. 36: | V V V S N G G K S S N F V R | K T N K N - R - - - | D M P L I D S D V F R V P - | P G Y N A P Q Q V H I T Q G D |
| Arabidopsis1 | SEQ. ID NO. 37: | T L P T T L D G P E K P L T | R R I E E P S H F R | D D L P M D H L R K R N V | S S D F P E D S A L A L S S T |
| Arabidopsis2 | SEQ. ID NO. 38: | T L P T T L D G P E K P L T | R R I E E P S H F R R | D D L P M D H P R L R N V | S S D F P E D S A L A L S S T |
| Arabidopsis3 | SEQ. ID NO. 39: | S L P S T L D G P R V P V T V | P L D T S L E R | D L P M D H P R I V R R - | V I G F P E D T S L A L H S S |
| SOYBEAN, PATENT | SEQ. ID NO. 40: | H L P S T L E I G P P D P V T V P | F D I P I A L E R | D L P E T | | |
| Wheat bran, N- | SEQ. ID NO. 41: | E P A S L L T G P S R L P V T V | G V A | D P R V R R - | V I G F E E Q I S S H S S | |

Fig. 8B.

|  | | 10 | 20 |
|---|---|---|---|
| Kidney bean | SEQ. ID NO. 42: | T P R Q T G L D - V R | Y T F G L I G D H |
| Arabidopsis1 | SEQ. ID NO. 43: | T M P K S T S E N P H | R E V V A G D L |
| Arabidopsis2 | SEQ. ID NO. 44: | T L P L P S K D A V D | K T A F V G D E |
| Arabidopsis3 | SEQ. ID NO. 45: | T M P F V S S P V P G | R H A V V G D E |
| Wheat bran, frag | SEQ. ID NO. 46: | M X A V G S S P G | R H A V E G D E |

Fig. 8C.

|  | | 10 | 20 |
|---|---|---|---|
| Kidney bean | SEQ. ID NO. 47: | V E S S M S A N G - - - - - - - - - | R G T P P Q E K |
| Arabidopsis1 | SEQ. ID NO. 48: | - - - - - - - S M S A M G - - - - - - - - - | - - - T P A D Q V |
| Arabidopsis2 | SEQ. ID NO. 49: | M E G A V D V N N T G K S M D T L E V S | K S A E Q L |
| Arabidopsis3 | SEQ. ID NO. 50: | M E G A V I A D - - - - - - - - - - - - - - | - - - X S X Q V |
| Wheat bran | SEQ. ID NO. 51: | M E X X V X D V X - - - - - - - - - - - - - | - - - X S X Q X |

POLYNUCLEOTIDES ENCODING PHYTASE POLYPEPTIDES

FIELD OF THE INVENTION

The present invention relates to isolated polypeptides having phytase activity, recombinant DNA sequences encoding such polypeptides, methods of producing such polypeptides and the use of said polypeptides in transgenic plants.

BACKGROUND OF THE INVENTION

Phytate is the major storage compound of phosphate in plant seeds and binds up to 80% of the total phosphate content in cereal grains (Eeckhout and Depaepe, 1994). It consists of a six-carbon ring with six phosphate groups attached. The negative charge is balanced by cations of magnesium, calcium among others. Together they form large crystals that are stored within the aleurone embryo or the endosperm of the seed.

Monogastric animals generally are not able to degrade the phytate present in the feed and the phosphate compound is thus, through the manure, administered to the environment. This leads to eutrophication of lakes, streams and the coastal sea, which results in increased growth of algae and in the end to sub-oxygen regimes and the death of aquatic life. For people with unbalanced diets as seen in many undeveloped countries the insufficient digestion of phytate is a severe nutritional problem, particularly because it is sequestering zinc and iron from uptake. The formation of insoluble aggregates of phytate with important minerals as zinc and iron as well as with proteins leads to poor digestibility of all the agents.

The scientific interest in phytate and its metabolic enzymes goes back more than a century, though it probably received the most attention from the general public in the early seventies. With the reintroduction of vegetable diets and wholemeal bread the degradation of phytate became a problem for human nutrition in the western world. Today phytate related concerns in the western world involves the negative effects on the environment caused by the intensive production of fish, pigs and poultry.

Phytate is the trivial name for the mixed salt of 1,2,3,4,5,6 myo-inositol-hexakisphosphate or phytic acid ($InsP_6$). Myo-inositol is synthesised from D-glucose via three enzymatic steps, a) hexokinase (EC 2.7.1.1), b) 1L-myo-inositol 1-phosphate synthase (EC 5.5.1.4) and c) myo-inositol 1-phosphate phosphatase (Loewus and Murthy, 2000).

Phytate ($InsP_6$) is believed to function as an effective storage compound in the seed of both phosphate and essential cations, especially potassium and magnesium. The inositol moiety, the phosphate groups as well as the chelated cations are believed to be utilised by the growing seedling.

Where ($InsP_6$ in the plant cells have been assigned a pure storage function and as a precursor of the lower InsP, recent reports have shown $InsP_6$ to act as a signalling molecule (Voglmaier et al., 1992), (Larsson et al., 1997) in animal systems, in yeast (York et al., 1999) and in plants (Munnik et al., 1998), (Muir and Sanders, 1997)

Phytases are a group of phosphatases that catalysis the stepwise removal of ortophosphate from phytate. Phytase enzymes are classified into two groups according to the initial position of hydrolysis. All the fungal phytases investigated as well as the novel phytases from *Bacillus subtilis* and *B. amyloliquefaciens* (Kerovuo et al., 1998 & 2000; Kim et al., 1998) initiate the hydrolysis of phytate at position 3 (EC 3.1.3.8) and catalyse the reaction:

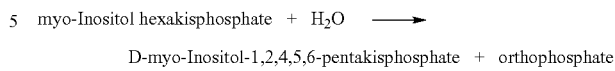

(The *Bacillus* enzyme is stated in the EMBL accession as 3-phytase but it has not been published elsewhere). The plant phytases as well as the enzyme from *E. coli* are 6-phytases (EC 3.1.3.26) and catalyse the reaction:

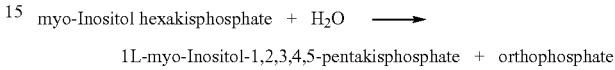

In this instance the L-configuration is used and the removed phospho-group in the latter reaction scheme is situated at position 4 when the D-configuration is assigned.

Most phytases identified are enzymes that accept a broad range of substrates and as such, phytases are a rather loosely defined subclass of phosphatases.

Numerous phytase enzymes hav been characterised from fungal, bacterial, animal and plant sources (Dvorakova, 1998). However, microbiel phytase enzymes are by far the best known. These include *Aspergillus niger* PhyB (Ehrlich et al., 1993), *A. fumigatus* (Ullah and Dischinger, 1993), *A. niger* PhyA (van Hartingsveldt et al., 1993), *A. niger w. awamori* (Piddington et al., 1993), *A. terreus* (Mitchell et al., 1997), *A. ficcum* (Ullah and Dischinger, 1993), *Emericella nidulans* (*Aspergillus nidulans*) (Mitchell et al., 1997), the heat tolerant *Talaromyces thermophilus* (Pasamontes et al., 1997), *E. coli* (Jia et al., 1998), *Bacillus* sp. (Kim et al., 1998) and *Bacillus subtilis* (Kerovuo et al., 1998).

Among plants phytase activity from wheat, rye, spelt, oat, rice and maize have all been subjected to purification and characterisation procedures. Phytases have been characterised from different plant tissues but only the exceptional alkaline phytase from lily pollen has phytate as the sole substrate (Scott and Loewus, 1986; Baldi et al., 1988; Barrientos et al., 1994).

In 1997 the first plant phytase was cloned from *Zea maize* (Maugenest et al., 1997). This enzyme was initially purified in 1993 (Laboure et al., 1993) and was described as a homo-dimer of a 38 kD polypeptide. An expression library was screened with antibodies raised against the purified protein and this lead to the identification of a full-length cDNA clone (phyS11). Two peptide sequences determined from the purified maize enzyme were encoded by the cDNA clone. The phyS11 clone was expressed in *E. coli* and a polypeptide with the same migration, when using SDS-PAGE and native-PAGE, as the maize phytase was obtained. However, no phytase activity associated with the heterologous polypeptide could be detected, even when the *E. coli* expressed protein was applied in 10 times higher concentrations than the detection level of the native enzyme activity (Maugenest et al., 1997). Neither has genetic transformation of maize with phyS11 constructs resulted in expression of an active phytase enzyme (P. Perez Limagrain, pers. Comm.).

The soybean phytase purified to apparent homogeneity from 10-day-old germinating cotelydons (Gibson and Ullah, 1988) is a monomeric enzyme with a native molecular w ight of 50 kD and it migrat s as two bands of 59 and 60 kD during SDS-PAGE (see tabl 1.). The enzyme activity is strongly inhibited by phosphate and 0.5 μM phosphate renders the enzyme only 67% active (apparent $K_i$=18 μM). This implies that the enzyme activity is tightly regulated by product inhibition.

The soybean phytase is reportedly blocked N-terminally, but an internal 18 amino acid from the enzyme was published in a 1990 review (Gibson and Ullah, 1990). This sequence (MHADQDYCANPQKYNXAI (SEQ ID NO: 13)) matches 100% with the sequence of soybean β-amylase (result not shown).

Another, N-terminal, soybean phytase sequence was published in GB 2319030. The sequence disclosed in GB 2319030 is similar to enzymes of the purple acid phosphatases (PAP) family, however this is not described in the patent.

Phytase enzymes from wheat bran having an activity optimum at pH 5.0 were purified and studied in detail by Nagai and Funahashi in the early sixties (Nagai and Funahashi, 1962; Nagai and Funahashi, 1963). Ten years later Lim and Tate (Lim and Tate, 1971; Lim and Tate, 1973) further published the presence and partial purification of two wheat bran phytase enzymes that could be separated on DEAE-cellulose but with identical molecular weights of 47 kD. The two enzyme fractions F1 and F2 differed by their pH optimum for activity of 5.6 and 7.2, respectively. The phytase activity of fraction F1 with a pH optimum at 5.6 (Lim and Tate, 1973) had many similarities to the earlier described phytase activity (Nagai and Funahashi, 1963) with an optimum at about 5.0, but the F1 activity was inhibited by phosphate and the latter was not inhibited at all. The products from the hydrolysis of phytate by the F1 and F2 enzyme preparations were analysed (Lim and Tate, 1973) and it was found that although 6-phytase (the product being D-ins1,2,3,5,6) was the primary activity of both fractions, the F2 fraction also exhibited 5- and 2-phytase activity (Irving, 1980).

Nakano et al., 1999 purified and biochemically characterized two wheat phytase enzymes from the "Nourin 61" wheat variety. The N-terminal sequence of both enzymes were determined to be 13 amino acid residues long having one unknown amino acid. A Swiss-Plot database examination did not reveal homologue sequences. The inv ntors did not disclose any gene or cDNA sequences.

In 1997 Nakano et al. purifi d and biochemically characterized three N-terminal sequences from wheat bran isoenzymes. Homologue sequences, gene or cDNA sequences were not described.

Any PCR based cloning strategy requires both a forward and a reverse primer. The N-terminal amino acid sequence can potentially be used to construct a forward primer, but no specific reverse primer can be made. It is therefore necessary to use a strategy using one unspecific primer in combination with the specific forward primer. Although such strategies exist (WALK-PCR, TAIL-PCR) they do far from always prove successful and more importantly they have as an absolute requirement that at least two nested non-degenerate primers can be constructed from the known sequence, which is not possible from the N-terminal amino acid sequence published by Nakano et al. 1999. This is because of the high codon degeneracy of the amino acids present in the amino terminal polypeptide (N-terminal sequence of Nakano et al.). For example, the amino acids arginine, serine and leucine are each represented by six codons in the standard genetic code, while the amino acids valine, threonine, proline, glycine, alanine are represented by four codons each. Furthermore, the fourth residue from the N-terminal is unknown Xaa, which altogether means these amino acids constitute 12 of the 13 residues in the amino terminal polypeptide sequence. Reverse transcription coupled PCR, RT-PCR on mRNA is inefficient and by no means trivial for fragment sizes over 700 bases, thus demanding internal sequences for primer design.

Alternative strategies are based on hybridisation screening of cDNA or genomic libraries, but a highly degenerate oligonucleotide of a maximum of 39 bases is not sufficient to do this Although it has been the aim of several researchers to obtain phytase sequence information from cereals, such as wheat and barley, it is not until now that an isolated phytase from wheat is presented, and specific wheat phytase sequences are disclosed along with cloned wheat and barley phytase encoding nucleotide sequences.

SUMMARY OF THE INVENTION

Accordingly, it is an object of the present invention to provide a phytase capable of being produced in large amounts.

In one aspect of the present invention a polypeptide having affinity for the substrate phytate (1,2,3,4,5,6 myo-inositol-hexakisphosphate, phytic acid), comprising an amino acid sequence as given in SEQ ID NO: 1 or an equivalent thereof, having a sequence identity of SEQ ID NO: 1 of at least 70% and at least one or more of the amino acid sequences as given in SEQ ID NO: 2, SEQ ID NO: 3, SEQ ID NO: 4, SEQ ID NO: 5, SEQ ID NO: 6, SEQ ID NO: 8, SEQ ID NO: 10, or SEQ ID NO: 13, or an equivalent thereof having a sequence identity with SEQ ID NO: 2, SEQ ID NO: 3, SEQ ID NO: 4, SEQ ID NO: 5, SEQ ID NO: 6, SEQ ID NO: 8, SEQ ID NO: 10, or SEQ ID NO: 13 of at least 70% is provided.

Further, the invention relates to a DNA fragment (SEQ ID NO.:11, and SEQ ID NO.:12) encoding said polypeptides and cDNA fragments (SEQ ID NO.:9) encoding said polypeptides.

Additionally, an expression cassette comprising said DNA fragments is described by the invention.

It is furthermore an object of the present invention to provide for a cell which is capable of expressing a polypeptide and which is transformed with an expression cassette as defined by the invention.

Furthermore, it is an object of the invention to provide a method of producing a polypeptide having affinity for the substrate phytate (1,2,3,4,5,6 myo-inositol-hexakisphosphate, phytic acid) comprising the steps of:

short time extraction of the polypeptide, obtaining an extract, subjecting the extract to purification steps, purifying the polypeptide from said extract, obtaining the polypeptide.

In an additional embodiment of the present invention a method of producing a polypeptide having affinity for the substrate phytate (1,2,3,4,5,6 myo-inositol-hexakisphosphate, phytic acid), wherein a cell which contains a recombinant expression vector comprising a DNA fragment encoding a polypeptide as defined above, is cultured in a suitable medium under conditions which promote the expression of the polypeptide, and where the polypeptide is recovered from the culture is provided for.

The present invention also relates to a product obtained by the methods as defined above and the invention describes the use of the polypeptides as defined by the invention.

Another object of the present invention is disclosing a transgenic plant or part thereof, wherein said plant or part thereof have been genetically modified to comprise a polypeptide as defined in by the invention.

BRIEF DESCRIPTION OF THE DRAWINGS

FIG. 8: ClustalW formatted alignment of the A) N-terminal or B) and C) internal fragment of the translated sequence of three putative PAP gene sequences from *A. thaliana* with the wheat bran phytase amino acid sequences which were obtained as described on pages 37 to 38. The kidney bean sequence is included for comparison and the numbers of residues for each of the fragments, when referring to the kidney bean sequence are: A) $Val_{16}$-$Asp_{63}$, B) $Thr_{145}$-$Leu_{163}$, and C) $Val_{276}$-$Tyr_{290}$. Accession numbers are: kidney bean CAA04644, *Arabidopsis*1 ACC04486, *Arabidopsis*2 CAB36834, *Arabidopsis*3 AC012395_20.

DETAILED DESCRIPTION OF THE INVENTION

Figure 1:
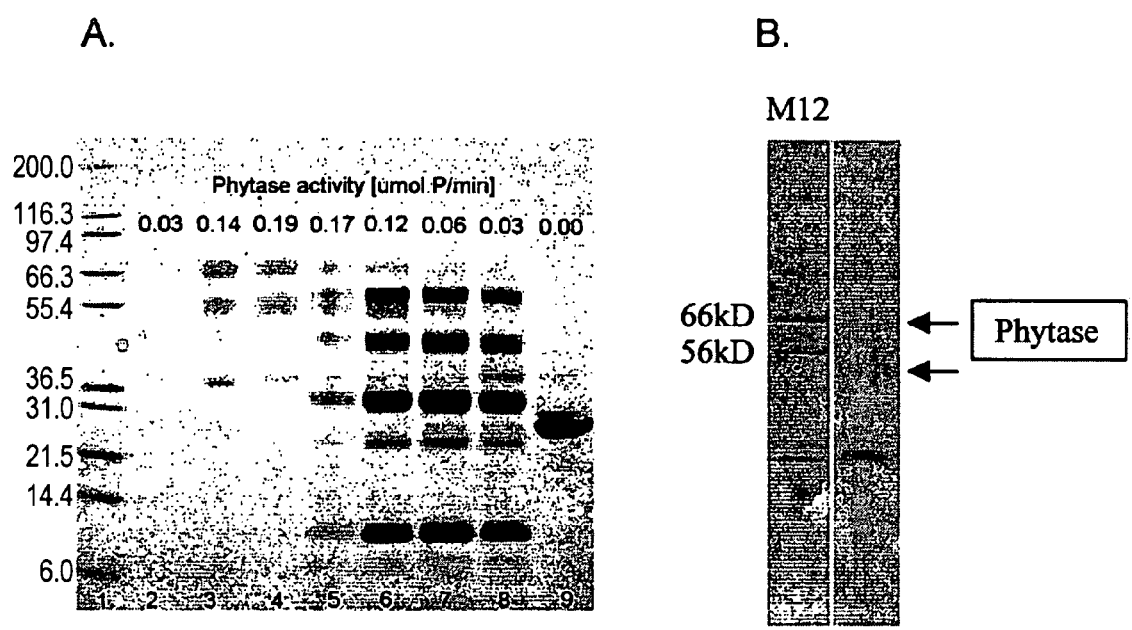
FIG. 1: A) shows the SDS-PAGE separation of proteins in the fractions from gelfiltration. Lane 2–9: 100 µl of each fraction 13–20, lane 1: M12 molecular weight standards loaded with approximately 0.5 µg protein in each band. The phytase activity of the fractions is given in the top of the lanes. B) is the visualisation by silver staining gel after SDS-PAGE of the pool of highly purified wheat bran phytase. N-terminal amino acid sequence and tryptic mass fingerprints have been obtained for several of the visible bands in lane 2. The two (broad) high MW and the two low MW bands each has identical N-terminal sequences. The lower peptides have been identified as γ-conglutin homologues (Johansen and Rasmussen, in prep). The upper two bands are the wheat bran phytase. M12 molecular weight standards.
Figure 2:
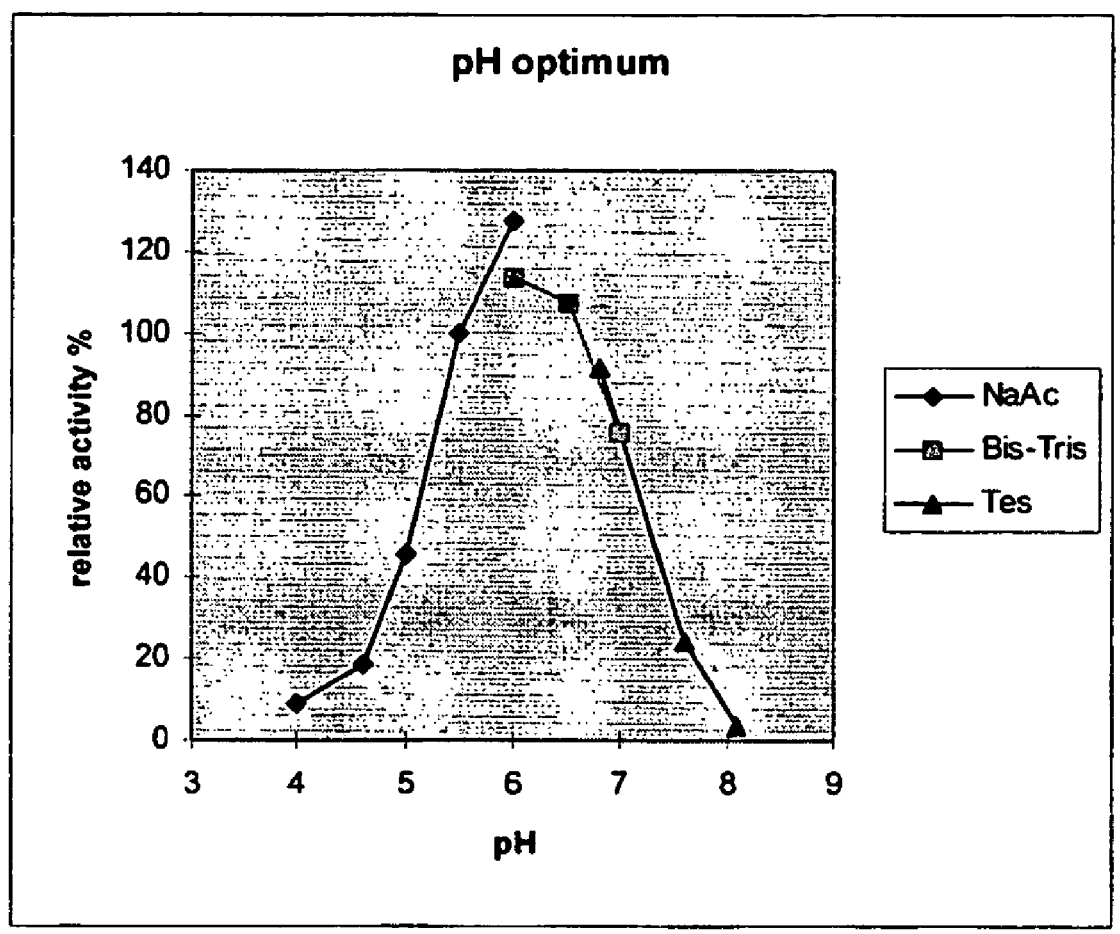
FIG. 2: shows a pH optimum curve for the highly purified wheat bran phytase. Buffers used are marked at different pH-intervals as indicated in the legend.
Figure 3:
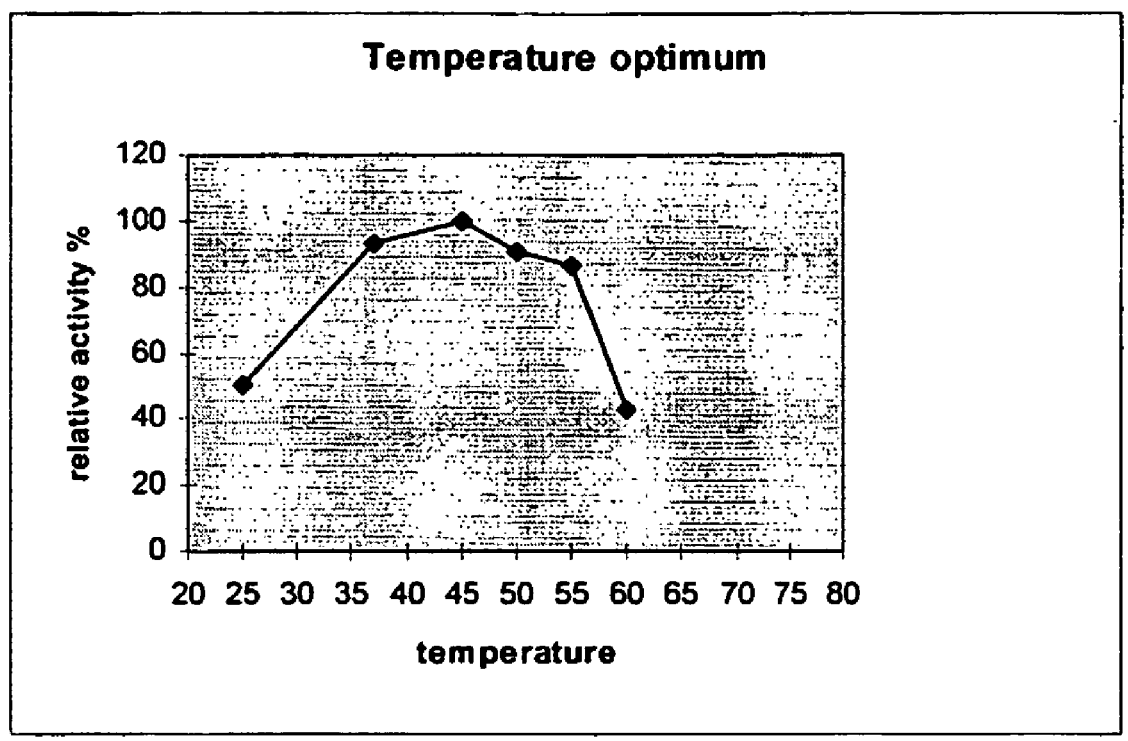
FIG. 3: shows a temperature optimum curve for wheat bran phytase.

The present invention relates to a phytase polypeptide and DNA fragments encoding a phytase polypeptide, in particular the invention discloses the production and isolation of a wheat and/or barley phytase. However, the invention is not limited to a phytase isolated from wheat, but concerns any phytase having the characteristics described by the invention. By the term phytase is meant a polypeptide as described in the introductory part having affinity for phytate. The phytase may have affinity for other substrates as well, as long as the phytate affinity is of an adequate size. The phytate affinity may be examined by using the method described in the examples under purification of wheat bran phytase. Thus a polypeptide or enzyme having affinity for phytate is any polypeptide or enzyme having phytate affinity and being capable of effecting the liberation of inorganic phospate or phosphorous from various myo-inositol phosphates. Examples of such myo-inositol phosphates (phytase substrates) are phytic acid and any salt thereof, such as sodium phytate or potassium phytate or mixed salts, or any stereoisomer of the mono-, di-, tri-, tetra- or penta-phosphate of myo-inositol.

The definition of "a polypeptide or enzyme" also includes fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides in frame and ensuring that expression of the fused polypeptide is controlled by the same promoter(s) and terminator. The polypeptide is preferably an isolated polypeptide, which is meant to mean a polypeptide being essentially free of other non-phytase polypeptides, such as at least 20% pure, preferably at least 40% pure, more preferably at least 60% pure, such as at least 80% pure, more preferably at least 90% pure, more preferably at least 95% pure as determined by SDS-PAGE.

In the context of the present invention any amino acid(s) designated: Xaa as mentioned in the amino acid sequence listings in the present text are defined as being any amino acid.

In one embodiment of the present invention the polypeptide is a phytase having affinity for phytate, comprising an amino acid sequence as given in SEQ ID NO: 1 or an equivalent thereof having a sequence identity with SEQ ID NO: 1 of at least 70%, such as 80% and at least one or more of the amino acid sequences as given in SEQ ID NO: 2, SEQ ID NO: 3, SEQ ID NO:4, SEQ ID NO:5, SEQ ID NO: 8, SEQ ID NO: 10, or SEQ ID NO:12, or an equivalent thereof having a sequence identity with SEQ ID NO: 2, SEQ ID NO:3, SEQ ID NO:4, SEQ ID NO: 6, SEQ ID NO: 8, SEQ ID NO:9, or SEQ ID NO:12 of at least 70%, such as at least 80%, for example at least 85%, such as at least 90%, for example at least 95%.

The equivalent may be obtained by addition, substitution or deletion of at least one amino acid.

A functional equivalent of a polypeptide of the invention is to be understood as any part (or fragment) or any mimic having affinity for phytate. A "functional equivalent" is defined as:

i) equivalents comprising an amino acid sequence capable of being recognised by an antibody also capable of recognising the predetermined amino acid sequence, and/or
ii) equivalents comprising an amino acid sequence capable of binding to a receptor moiety also capable of binding the predetermined amino acid sequence, and/or
iii) equivalents having at least a substantially similar or higher binding affinity to phytate as at least a polypeptide of the invention comprising said predetermined amino acid sequence.

According to the present invention a functional quivalent of a polypeptide of the invention or fragments thereof may be obtained by addition, substitution or deletion of at least one amino acid in the polypeptide sequence.

Examples of equivalents comprising one or more conservative amino acid substitutions including one or more conservative amino acid substitutions within the same group of predetermined amino acids, or a plurality of conservative amino acid substitutions, wherein each conservative substitution is generated by substitution within a different group of predetermined amino acids.

In another embodiment of the invention the polypeptide comprises an N-terminal amino acid sequence as described in SEQ ID NO:1, or an equivalent thereof having a sequence identity with SEQ ID NO:1 of at least 70% such as 80% and at least one or more of the amino acid sequences as given in SEQ ID NO: 2, SEQ ID NO: 3, SEQ ID NO: 4, SEQ ID NO: 5, SEQ ID NO: 6, SEQ ID NO: 8, SEQ ID NO: 10, or SEQ ID NO: 13, or an equivalent thereof having a sequence identity with SEQ ID NO: 2, SEQ ID NO: 3, SEQ ID NO: 4, SEQ ID NO: 5, SEQ ID NO: 6, SEQ ID NO: 8, SEQ ID NO: 10, or SEQ ID NO: 13 of at least 70%.

The equivalent may be obtained by addition, substitution or deletion of at least one amino acid.

A further embodiment relates to a polypeptide having an amino acid sequence as given in SEQ ID NO:1 or an equivalent thereof having a sequence identity with SEQ ID NO:1 of at least 70%, such as at least 80%, for example at least 85%, such as at least 90%, for example at least 95%. and an amino acid sequence as given in SEQ ID NO: 2 or an equivalent thereof having a sequence identity with SEQ ID NO:2 of at least 70%, such as at least 80%, for example at least 85%, such as at least 90%, for example at least 95%.

The equivalent may be obtained by addition, substitution or deletion of at least one amino acid.

In yet a further embodiment a polypeptide having an amino acid sequence of given in SEQ ID NO:1 or an equivalent thereof having a sequence identity with SEQ ID NO:1 of at least 70%, such as at least 80%, for example at least 85%, such as at least 90%, for example at least 95%. and an amino acid sequence as given in SEQ ID NO: 3 or an equivalent thereof having a sequence identity with SEQ ID NO:3 of at least 70%, such as at least 80%, for example at least 85%, such as at least 90%, for example at least 95%.

In another embodiment given in SEQ ID NO:1 or an equivalent thereof having a sequence identity with SEQ ID NO:1 of at least 70%, such as at least 80%, for example at least 85%, such as at least 90%, for example at least 95%. and an amino acid sequence as given in SEQ ID NO:4 or an equivalent thereof having a sequence identity with SEQ ID NO:4 of at least 70%, such as at least 80%, for example at least 85%, such as at least 90%, for example at least 95%.

The invention also relates to a polypeptide having an internal amino acid sequence in given in SEQ ID NO:1 or an equivalent thereof having a sequence identity with SEQ ID NO:1 of at least 70%, such as at least 80%, for example at least 85%, such as at least 90%, for example at least 95%. and an amino acid sequence as given in SEQ ID NO: 6 or an equivalent thereof having a sequence identity with SEQ ID NO:5 of at least 70%, such as at least 80%, for example at least 85%, such as at least 90%, for example at least 95%.

In a further embodiment the invention discloses a polypeptide having an amino acid sequence as given in SEQ ID NO:1 or an equivalent thereof having a sequence identity with SEQ ID NO:1 of at least 70%, such as at least 80%, for example at least 85%, such as at least 90%, for example at least 95%. and an amino acid sequence as given in SEQ ID NO: 8 or an equivalent thereof having a sequence identity with SEQ ID NO:7 of at least 70%, such as at least 80%, for example at least 85%, such as at least 90%, for example at least 95%.

In yet another embodiment the invention discloses a polypeptide having an amino acid sequence as given in SEQ ID NO:1 or an equivalent thereof having a sequence identity with SEQ ID NO:1 of at least 70%, such as at least 80%, for example at least 85%, such as at least 90%, for example at least 95%. and an amino acid sequence as given in SEQ ID NO: 10 or an equivalent thereof having a sequence identity with SEQ ID NO:9 of at least 70%, such as at least 80%, for example at least 85%, such as at least 90%, for example at least 95%.

In a further embodiment the invention discloses a polypeptide having an amino acid sequence as given in SEQ ID NO:1 or an equivalent thereof having a sequence identity with SEQ ID NO:1 of at least 70%, such as at least 80%, for example at least 85%, such as at least 90%, for example at least 95%. and an amino acid sequence as given in SEQ ID NO: 13 or an equivalent thereof having a sequence identity with SEQ ID NO:12 of at least 70%, such as at least 80%, for example at least 85%, such as at least 90%, for example at least 95%.

In a preferred embodiment of the invention the polypeptide is having an amino acid sequence of a wheat phytase comprising sequences as given in SEQ ID NO:1 or an equivalent thereof having a sequence identity with SEQ ID NO:1 of at least 70%, such as at least 80%, for example at least 85%, such as at least 90%, for example at least 95%. and an amino acid sequence as given in SEQ ID NO: 2 or an equivalent thereof having a sequence identity with SEQ ID NO:2 of at least 70%, such as at least 80%, for example at least 85%, such as at least 90%, for example at least 95%. and a polypeptide having an amino acid sequence as given in SEQ ID NO:3 or an equivalent thereof having a sequence identity with SEQ ID NO:3 of at least 70%, such as at least 80%, for example at least 85%, such as at least 90%, for example at least 95%.

In a further preferred embodiment the polypeptide is having an amino acid sequence of a wheat phytase comprising sequences as given in SEQ ID NO:1 or an equivalent thereof having a sequence identity with SEQ ID NO:1 of at least 70%, such as at least 80%, for example at least 85%, such as at least 90%, for example at least 95%. and an amino acid sequence as given in SEQ ID NO: 5 or an equivalent thereof having a sequence identity with SEQ ID NO:4 of at least 70%, such as at least 80%, for example at least 85%, such as at least 90%, for example at least 95%. and a polypeptide having an amino acid sequence as given in SEQ ID NO:3 or an equivalent thereof having a sequence identity with SEQ ID NO:3 of at least 70%, such as at last 80%, for example at least 85%, such as at least 90%, for example at least 95%.

In yet a further preferred embodiment the polypeptide is having an amino acid sequence of a wheat phytase comprising sequences as given in SEQ ID NO:1 or an equivalent thereof having a sequence identity with SEQ ID NO:1 of at least 70%, such as at least 80%, for example at least 85%, such as at least 90%, for example at least 95%. and an amino acid sequence as given in SEQ ID NO: 6 or an equivalent thereof having a sequence identity with SEQ ID NO:5 of at least 70%, such as at least 80%, for example at least 85%, such as at least 90%, for example at least 95%. and a polypeptide having an amino acid sequence as given in SEQ ID NO:3 or an equivalent thereof having a sequence identity with SEQ ID NO:3 of at least 70%, such as at least 80%, for example at least 85%, such as at least 90%, for example at least 95%.

In yet another embodiment the invention discloses a DNA molecule having a nucleotide sequence as given in SEQ ID NO:8 or an equivalent thereof having a sequence identity with SEQ ID NO:8 of at least 70%, such as at least 80%, for example at least 85%, such as at least 90%, for example at least 95%. is provided for. The equivalent may be obtained by addition, substitution or deletion of at least one nucleotide.

The invention also relates to a polypeptide having an amino acid sequence as given in SEQ ID NO:9 or an equivalent thereof having a sequence identity with SEQ ID NO:9 of at least 80%, such as 90% is provided for. The equivalent may be obtained by addition, substitution or deletion of at least one amino acid.

In a further aspect a polypeptide having an amino acid sequence as given in SEQ ID NO:12 or an equivalent thereof having a sequence identity with SEQ ID NO:12 of at least 80%, such as 90% is provided for. The equivalent may be obtained by addition, substitution or deletion of at least one amino acid.

In a further embodiment the invention discloses a DNA molecule having a nucleotide sequence as given in SEQ ID NO: 11 or an equivalent thereof having a sequence identity with SEQ ID NO: 11 of at least 80%, such as 90% is provided for. The equivalent may be obtained by addition, substitution or deletion of at least one nucleotide.

Additionally, the invention discloses a DNA molecule having a nucleotide sequence as given in SEQ ID NO: 12 or an equivalent thereof having a sequence identity with SEQ ID NO: 12 of at least 80%, such as 90% is provided for. The equivalent may be obtained by addition, substitution or deletion of at least one nucleotide.

The DNA molecules of the invention encoding a phytase polypeptide as given in SEQ ID NO: 9, 11 and 12 may be modified to optimise the codon usage for improved expression in a particular organism, such as bacteria, fungi, and plants.

When the amino acid sequences of the invention comprise a substitution of one amino acid for another, such a substitution may be a conservative amino acid substitution as defined herein above. Sequences according to the present invention may comprise more than one such substitution, such as e.g. two conservative amino acid substitutions, for example three or four conservative amino acid substitutions, such as five or six conservative amino acid substitutions, for example seven conservative amino acid substitutions. Substitutions can be made within any one or more groups of predetermined amino acids. Conservative substitutions may be introduced in any position of a preferred predetermined polypeptide or fragment thereof. It may however also be desirable to introduce non-conservative substitutions, particularly, but not limited to, a non-conservative substitution in any one or more positions.

The addition or deletion of an amino acid may be an addition or deletion of from 2 to preferably 7 amino acids, such as from 2 to 5 amino acids, for example from 2 to 3 amino acids. However, additions of more than 7 amino acids, such as additions from 8 to 10 amino acids, are also comprised within the present invention.

In the context of the invention the term a functional equivalent relates to a sequence or a polypeptide comprising a sequence possessing a corresponding property as the polypeptides comprising the sequences mentioned in the present invention, but wherein one or more amino acids have been substituted with others. Preferably a functional equivalent contains substitutions, i.e. where one or more amino acids are substituted by an amino acid having similar properties.

The amino acids suitable for substitutions may include those having functionally similar side chains. For example, hydrophobic residues: e.g. glycine, alanine, valine, leucine, isoleucine and methionine may replace another such residue. Similarly, conservative substitutions may involve interchanging hydrophilic residues: (e.g.: arginine and lysine, glutamine and asparagine, threonine and serine), basic reduces (e.g., lysine, arginine and histidine), and/or acidic residues (e.g., aspartic acid and glutamic acid). Functional equivalents may also, or alternatively, be modified by for example the deletion or addition of amino acids, or the chemical modification of amino acids, as long as the function of the polypeptide is preserved.

The isolated wheat bran polypeptide comprising one or more sequences of the present invention, including any variants and functional equivalents thereof, may in one embodiment comprise less than 250 amino acid residues, such as less than 225 amino acid residues, for example less than 200 amino acid residues, such as less than 175 amino acid residues, for example less than 150 amino acid residues, such as less than 125 amino acid residues, for example less than 100 amino acid residues.

In a more preferred embodiment the polypeptide comprises at least two of the sequences described. Preferably the polypeptide comprises SEQ ID NO:1 or an equivalent thereof and at least one of the other sequences or equivalents thereof.

The equivalents are at least 70% identical with the sequences shown herein, such as at least 75% identical, preferably at least 80% identical, such as at least 85% identical, such as at least 90% identical, for example at least 95% identical.

Where a particular polypeptide is said to have a specific percent identity to a reference polypeptide of a defined length. Thus, a polypeptide that is 50% identical to a reference polypeptide that is 20 amino acids long can be a 10 amino acid polypeptide that is completely identical to a 10 amino acid long portion of the reference polypeptide. It might also be a 20 amino acid long polypeptide which is 50% identical to the reference polypeptide over its entire length. The degree of identity between the sequences of the invention and their equivalents may be determined by commercially available computer software, such as MacVector.

In yet a further embodiment of the invention the polypeptide is capable of binding a monoclonal anti-body raised against a polypeptide having the sequence of SEQ ID NO: 1 and at least one or more of the amino acid sequences as given in SEQ ID NO: 2, SEQ ID NO: 3, SEQ ID NO: 5, SEQ ID NO: 6, SEQ ID NO: 8, SEQ ID NO: 10, or SEQ ID NO: 13.

According to the invention monoclonal antibodies may also be raised against a polypeptide comprising the SEQ ID NO:1 and at least one or more of the amino acid sequences as given in SEQ ID NO: 2, SEQ ID NO: 3, SEQ ID NO: 5, SEQ ID NO: 6, SEQ ID NO: 8, SEQ ID NO: 10, or SEQ ID NO: 13.

In a preferred embodiment the polypeptide comprise one or more of the sequences listed above and bind the antibody as defined above.

The polypeptide of the invention has various biochemical characteristics. Accordingly, the denatured polypeptide of the invention preferably has a molecular weight of 50–75 kDa, preferably 53–70 kDa, more preferable 55–68 kDa as determined by SDS-PAGE (Sodium dodecyl sulphate Poly-Acrylamide Gel Electrophoresis).

Furthermore, the polypeptide of the invention has a native molecular weight of 35–70 kDa as determined by gelfiltration, such as 40–66, for example 45–60.

The polypeptide preferably has a substrate affinity of 0.05–0.50 mM, such as 0.08–0.45, for example 0.10–0.35, such as 0.14–0.25.

The polypeptide preferably has a substrate affinity of 0.002–0.50 mM, such as 0.08–0.45, for example 0.10–0.35, such as 0.14–0.25. In one aspect of the invention the polypeptide has a $V_{max}$ of 600–1000 U/mg, such as 700–900 U/mg, for example 750–850 U/mg. $V_{max}$ is defined as the maximum reaction velocity, i.e. the maximal velocity obtained when all of the phytase is in the form of the phytase-phytate complex. The substrate affinity and the reaction velocity may be determined by designing classical biochemical experiments, and measure the concentration of the liberated phosphate as described below in the experimentals section. The enzyme activity may be determined by measuring the amount of released phosphate through the colour intensity of a phosphate complex such as the yellow colour of the phosphate-molybdate-vanadate complex. Alternatively the amount of low r myo-inositol phosphates generated by the enzyme activity may be quantified by HPLC-based methods.

In another aspect of the invention the polypeptide has an isoelectric point of between 5.0–8.0, such as between 5.5–7.0.

The polypeptide according to the invention preferably has a pH optimum of between 4 and 8, preferably between 5–7. This refers to the polypeptide having an optimal activity in the above ranges of pH values.

Also, the polypeptide of the invention, has an optimal activity at a temperature between 30–65° C., preferably between 35–60° C., and more preferably between 40–55° C. In the present context the term "optimal activity" is defined as the optimal rate of which the enzyme/polypeptide of the invention converts it substrate myo-inositol-1,2,3,4,5,6-hexakisphosphate or phytic acid into inorganic phosphate and lower myo-inositol-phosphates, such as D-myo-inositol-1,2,3,5,6-hexakisphosphate, D-myo-inositol-1,2,5,6-hexakisphosphate among others. In one embodiment of the invention the polypeptide exhibits 6-phytase activity (EC 3.1.3.26).

In a preferred embodiment the polypeptide has a thermostability that is sufficient to withstand the heat processing of fodder. This can be achieved by random mutagenesis and selection in thermostabile microorganisms, or by point mutation of selected amino acids to achieve better thermostability of the polypeptide with the purpose of maintaining sufficient residual activity for down stream use.

Another important purpose of the invention is to provide a DNA fragment encoding a polypeptide according to the invention. The invention also relates to a cDNA fragment encoding the polypeptide of the invention.

The composition of the polypeptide sequences of the invention is such that isolation of a DNA molecule encoding a phytase polypeptide according to the invention has proved difficult even to someone skilled in the art. This is because of the high codon degeneracy of the amino acids present in the amino terminal polypeptide (SEQ ID NO.:1) of the invention. For example, the amino acids arginine and leucine are both represented by six codons in the standard genetic code, while the amino acids valine, threonine, proline, glycin , alanine are represented by four codons each. Together these amino acids constitute 12 of the 15 residues in the amino terminal polypeptide sequence.

In a preferred embodiment of the invention a DNA molecule encoding a polypeptide according to the invention is therefore isolated using a degenerate oligonucleotide primer derived from reverse translation of the internal polypeptide of the invention (SEQ ID NO.:2) and an oligonucleotide primer annealing to DNA sequences of a barley EST clone (acc. No. BE602374). This clone can be identified as putatively encoding a purple acid phosphatase by its degree of identity to the carboxy-terminal part of the *Arabidopsis thaliana* putative purple acid phosphatase (acc. No. AAF20233), which itself shows partial conservation of the polypeptide sequences of the invention (see FIG. 8). Employing the polymerase chain reaction (PCR) using these oligonucleotide primers and genomic DNA isolated from wheat as template will result in isolation of a DNA molecule encoding the carboxy terminal part of the polypeptide of the invention. DNA fragments encoding the amino-terminal part of the polypeptide of the invention is isolated by sequential PCR on restriction digested genomic wheat DNA to which an adapter has been ligated using nested primers annealing to the adapter and the carboxy-terminal part of the polypeptide of the invention.

In one embodiment of the invention the complete genomic DNA fragment or parts of it is preferably isolated using PCR with oligonucleotide primers from the amino- and carboxy-terminal parts on genomic DNA from wheat or barley.

In a further embodiment the complete cDNA fragment of the invention or parts of it is preferably isolated using RT-PCR with oligonuceotide primers from the amino- and carboxy-terminal parts on RNA from immature wheat or barley kernels.

Furthermore, the DNA fragment of the invention may be subjected to cloning procedures. This may involve excision and isolation of a desired nucleic acid fragment comprising the nucleic acid sequence encoding the polypeptide, insertion of the fragment into a vector molecul , and incorporation of the recombinant vector into a host cell where multiple copies or clones of the nucleic acid sequence will be replicated.

The nucleic acid sequence may be of genomic, cDNA, RNA, semisynthetic, synthetic origin, or any combinations thereof.

The invention further relates to a DNA construct comprising the polypeptide as defined by the invention and an expression cassette comprising the DNA construct. The expression vector carrying the DNA construct of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extra chromosomal entity, the replication of which is independent of chromosomal replication, for example a plasmid, a bacteriophage or an extra chromosomal element, mini chromosome or an artifical chromosome. Alternatively, the vector may be one which, when introduced into a host cell, is integrated into the host cell genome and replicated together with the chromosome(s) into which it has been integrated. Thus, the present invention further relates to a cell which is capable of expressing a polypeptide and which is transformed with an expression cassette as defined by the invention.

The cell of the invention either comprising a DNA construct or an expression vector according to the invention as defined above is advantageously used as a host cell in the recombinant production of a protein variant according to the invention. The cell may be transformed with the DNA construct, for example by integrating the DNA construct in the host chromosome. Integration is considered to be an advantage as the DNA fragment is more likely to be stably maintained in the cell. Alternatively, the cell may be transformed as described above for the expression vector.

According to the invention the host cell may be chosen from mammal, avian, insect or plant cells, or it may be selected from bacteria or fungi. The host cell is responsible for synthesising and expressing the polypeptide according to the invention and an expression cassette may transform the cell.

Preferably the host cell is a bacteria selected from gram positive bacteria, such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis*, or *Streptomyces lividans* or *Streptomyces murinus*, or a gram negative bacteria, such as *E. coli*.

More preferably the host cell of the present invention is of fungal origin and is selected among the species of *Saccharomyces* or *Schizosaccharomyces*, e.g. *Saccharomyces cerevisiae*. In a preferred embodiment of the present invention the fungus may advantageously belong to the species of *Aspergillus*, e.g. *Aspergillus oryzae* or *Aspergillus niger* or *Pichia*, e.g. *Pichia pastoris*. In a less preferred embodiment the species of *Fusarium*, e.g. *F. oxysporum* may be used as a host cell.

Most preferably the host cell is of plant origin, and may be selected from any plant, such as a plant cell from wheat, barley, rye, rye grass, spelt, oat, rice or maize.

Alternatively, the DNA fragment of the DNA construct may be prepared synthetically by established standard methods.

It is a purpose of the present invention to provide for a method of producing a recombinant polypeptide having affinity for the substrate phytate (1,2,3,4,5,6 myo-inositol-hexakisphosphate, phytic acid), wherein a cell which contains a recombinant expression vector comprising a DNA fragment encoding a polypeptide as defined by the invention, is cultured in a suitable medium under conditions which promote the expression of the polypeptide, and where the polypeptide is recovered from the culture.

According to the invention the polypeptide is being synthesised and expressed in host cells. This is achieved by culturing host cells capable of expressing a polypeptide in a suitable culture medium to obtain expression, and possibly secretion of the polypeptide. The polypeptide may be recovered from the culture medium or from the cells or from the cell culture as a whole.

Furthermore, the present invention describes a method of producing a wheat bran or barley polypeptide having affinity for the substrate phytate (1,2,3,4,5,6 myo-inositol-hexakisphosphate, phytic acid) comprising the steps of:

short time extraction of the polypeptide,
obtaining an extract,
subjecting the extract to purification steps,
purifying the polypeptide from said extract,
obtaining the polypeptide.

The plant material may be any plant material. In one embodiment of the invention the plant material selected are wheat roots. In a preferred embodiment of the invention the plant material selected are wheat seeds.

In another embodiment the plant material may be selected from barley roots. However, in a preferred embodiment the plant material selected may be from barley seeds.

Once the polypeptide of the invention has been extracted from the plant material chosen it is necessary to purify the polypeptide from the extract. According to the invention the purification of the polypeptide of the invention is performed by a combination of different biochemical separation methods. In a preferred embodiment of the invention the purification procedure is performed stepwise as follows: ammonium sulphate precipitation, filtration, dialysis, ion exchange chromatography, ultro-gel, resource S ion exchange, and Superose 12 gelfiltration. These are all well established techniques in the art of protein purification and leads to the stepwise separation of protein species in the extract based on hydrophobicity, charge, affinity towards hydroxyapatite and molecular size. The order of the individual purification steps of the invention may be any order of the above mentioned purification methods.

An essential feature of the purification process of the present invention is the short time span in which the purification is performed. Thus, in a preferred embodiment of the invention the extraction protocol is characterised by a short extraction time. It is desirable to have the extraction period being as short as possible to avoid proteolysis. In the context of the present invention a short time extraction may be a period of 60 minutes, such as 45 minutes, for example 30 minutes. Another important characteristic feature of the purification protocol of the present invention is the inclusion of only aqueous solvents (the detailed purification procedure is described below in the experimentals section).

Having obtained the polypeptide according to the invention a continuation of the method of producing a polypeptide defined by the invention and described above comprises the steps of:

exposing the polypeptide to epitope specific antibodies raised against said polypeptide,
assessing the specificity by Western blotting.

The epitope specific antibodies raised against the polypeptide may be raised by the means of conventional procedures. According to the invention a synthetic peptide corresponding to the amino acid sequence of the wheat polypeptide of the invention were conjugated to a carrier enzyme, such as the Keyhole limpet hemocyanin protein, and polyclonal antibodies against the polypeptide may be raised in for example a rabbit. By the term a "carrier protein" is a scaffold structure, e.g. a polypeptide or a polysaccharide, to which an immunogenic determinant is capable of being associated. When the synthetic polypeptide of the invention is obtained a carrier may be associated with the polypeptide. The carrier may be either non-conjugated or conjugated. When the carrier is conjugated, the polypeptide may be conjugated to said carrier, or the carrier may be conjugated to said polypeptide. The polypeptide may—in addition to a carrier—further comprise an adjuvant for increasing the efficacy of the composition. Any suitable adjuvant may be used in combination with the polypeptide/carrier composition. In the present context the term conjugated refers to an association formed between the polypeptide and a carrier. The association may be a physical association generated e.g. by the formation of a chemical bond, such as e.g. a covalent bond, formed between the polypeptide and the carrier.

When using the methods described by the invention products are obtained. The products of the invention relate to wheat bran polypeptides having affinity for phytate.

A very important aspect of the invention is the use of a polypeptide as defined in the invention.

In one aspect the polypeptide is used as an additive in animal feeds. The polypeptide of the invention may be applied to the feed, such as fodder-pellets. It is important that the phytase polypeptide added to the fodder has the desirable properties of a broad substrate specificity, a high specific activity and resistance towards proteolysis. Since the production of fodder-pellets is conducted under high temperatures it is an object of the invention to provide a thermostable phytase polypeptide. By adding phytase enzymes to animal feeds a reduction in the addition of phosphorous may be obtained, leading to more environmentally friendly animal feeds.

Applying the polypeptide of the invention as an additive in food for human consumption is also a concern. Phytate degradation is not merely a concern in relation to farm animals but also in relation to human nutrition.

A number of reports on anticancer effects of phytase have been published during the last few years. In an experiment on rat, it has been shown that when labelled phytase is given in the drinking water is rapidly taken up and distributed in the body. Here it leads to a 33.5% reduction in mammary tumor incidences as compared to a control group (Shamsuddin and Vucenik, 1999). The myo-inositol moiety itself have a similar effect on lung and liver carcinogenesis in mice and it is therefore suspected that a degree of phosphorylation or dephosphorylation of the inositol compounds must occur in the cells (Nishino et al., 1999). These reports are emphasising the importance of an effective degradation of phytate-aggregates in the food in order to improve the uptake of healthy and necessary food-components.

Application of fungal phytase enzymes in the preparation of foods for humans have been reported. The present invention thus stresses the use of wheat bran phytase according to the invention as an industrial processing enzyme.

In one embodiment of the invention the polypeptide of the invention is used to extract proteins from rice bran. The processing of rice bran to generate a protein isolate that may be used for e.g. the formulation of infant food is within the scope of the invention. The processing rate may increase significantly when incubation with the polypeptide of the invention is included in the procedure. Clearly, the present invention presents advantages in industrial applications, such as turning inexpensive wheat bran into high profit products.

In a further aspect the present invention relates to the generation of high-phytase rice. This aspect not only may improve phosphor and mineral but also protein digestibility. This is a crucial fact when attempting to raise the nutritional value of human diets in countries where rice is a major part of the diet. In such countries particularly zinc and iron deficiencies are major problems that the present invention may help alleviate.

Phosphorus is a limiting factor for plant growth in many parts of the world. Phosphorus is found in the soil both as an inorganic and organic form in the soils. The major part of the organic phosphate is inositol phosphates which is poorly or not utilized by many plant species. This is because the interaction of phytate with soil-matters renders inositol phosphates inaccessible for plant up-take, or the plant root does not provide mechanisms for the release and subsequent uptake of inositol phosphates. It is within the scope of the present invention to overcome this problem by extracellular secretion of wheat or barley phytase from roots of plants which have been transformed with a phytase gene of the invention. This will enable these plants to utilize phosphorus from inositol phosphates and or phytate and thereby sustain the plant growth organic phosphorus pools in the soil. The phytase DNA may be under control of a root specific promotor.

The wheat and barley phytase encoding nucleotide sequences according to the invention may allow for transformation of plants. The level of intrinsic phytase activity in many plants is relatively low compared to the phytate content, and not sufficient for adequate digestibility of phosphorus in monogastric animals. Thus, according to the invention the use of the polypeptide may be in a transgenic plant or part thereof. In a further aspect the invention relates to the use of a transgenic plant or part thereof, wherein said plant or part thereof have been genetically modified to comprise a polypeptide as defined in the invention. The expression of the wheat bran phytase and barley phytase could under the control of a seed specific promoter be synthesised and stored in large quantities in the mature grain. Wheat bran and barley phytases have the advantage of their natural design for storage in the seeds.

It is envisioned that the use of the polypeptide of the invention may be in any transgene plant for which it is desirable to obtain additional phytase activity.

The transgenic plant may be dicotyledonous or monocotyledonous, for short a dicot or a monocot. Of primary interest are such plants which are potential food or feed components and which comprise phytic acid. A normal phytic acid level of feed components is 0.1–30 g/kg, or more usually 0.5–25 g/kg, most usually 0.5–18 g/kg. Examples of monocot plants are grasses, such as meadow grass (blue grass, Poa), forage grass such as festuca, lolium, temperate grass, such as Agrostis, and cereals, e.g. wheat, oats, rye, barley, rice, sorghum and maize (corn).

Examples of dicot plants are legumes, such as lupins, pea, bean and soybean, and cruciferous (family Brassicaceae), such as cauliflower, oil seed rape (canola) and the closely related model organism *Arabidopsis thaliana*.

Preferably, the plant or plant part, e.g. the seeds, are ground or milled, and possibly also soaked before being added to the food or feed or before the use, e.g. intake, thereof, with a view to adapting the speed of the enzymatic degradation to the actual use. If desired, the enzyme produced by the plant may also be recovered from the plant. In certain cases the recovery from the plant is to be preferred with a view to securing a heat stable formulation in a potential subsequent pelleting process.

Examples of plant parts are stem, callus, leaves, root, fruits, seeds, tubers etc. But also any plant tissue is included in this definition.

Any plant cell, whatever the tissue origin, is included in the definition of plant cells above. Also included within the scope of the invention are the progeny of such plants, plant parts and plant cells. The skilled person will known how to construct a DNA expression construct for insertion into the plant in question, paying regard i.e. to whether the transcript should be expressed in a tissue specific way. Of relevance for this evaluation is the stability (pH-stability, degradability by endogenous proteases etc.) of the phytase in the expression compartments of the plant. The skilled artisan will also be able to select appropriate regulatory sequences such as promoter and terminator sequences, and signal or transit sequences if required (Tague et al, 1988).

The plant, plant part tc. can be transformed with the DNA construct using any known method. An example of such method is the transformation by a viral or bacterial vector such as bacterial species of th genus Agrobacterium genetically engineered to comprise the gene encoding the phytase of the invention. Also methods of directly introducing the phytase DNA into the plant cell or plant tissue are known in the art, e.g. micro injection and electroporation (Gasser et al, 1993; Potyrkus, 1990; Shimamoto et al, 1989), or particle bombardment (microscopic gold or tungsten particles coated with the transforming DNA) of embryonic calli or developing embryos (Christou, 1992; Shimamoto, 1994

Following the transformation, the transformants are screened by using any method known to the skilled person, following which they are regenerated into whole plants.

These plants etc. as well as their progeny then carry the phytase encoding DNA as a part of their genetic equipment. *Agrobacterium tumefaciens* mediated gene transfer is the method of choice for generating transgenic dicots (for review Hooykas & Schilperoort, 1992). The method of choice for generating transgenic monocots is particle bombardment.

Also, other systems for the delivery of free DNA into plants, include viral vectors (Joshi & Joshi, 1991), protoplast transformation via polyethylene glycol or electroporation (for review see Potyrkus, 1991), or microinjection of DNA into mesophyll protoplasts (Crossway et al., 1986).

In general, the cDNA or gene encoding the phytase of the invention is placed in an expression cassette (e.g. Pietrzak et al., 1986) consisting of a suitable promoter active in the target plant and a suitable terminator (termination of transcription). This cassette will be transformed into the plant as such in case of monocots via particle bombardment. In the case of dicots the expression cassette is placed first into a suitable vector providing the T-DNA borders and a suitable selection marker which in turn are transformed into *Agrobacterium tumefaciens*. Dicots will be transformed via the Agrobacterium harbouring the expression cassette and selection marker flanked by T-DNA following standard protocols (e.g. Akama et al., 1992). The transfer of T-DNA from *Agrobacterium* to the Plant cell has been recently reviewed (Zupan & Zambryski, 1995). Vectors for plant transformation via *Agrobacterium* are comm rcially available or can be obtained from many labs that construct such vectors (e.g. Deblaere et al., 1985; for review see Klee et al., 1987).

Available plant promoters: depending on the process under manipulation, organ- and/or cell-specific expression as well as appropriate developmental and environmental control may be required. For instance, it is desirable to express a phytase cDNA in maize endosperm etc. The most commonly used promoter has been the constitutive 35S-CaMV promoter Franck et al., 1980). Expression will be more or less equal throughout the whole plant. This promoter has been used successfully to engineer herbicide- and pathogen-resistant plants (for review see Stitt & Sonnewald, 1995). Organ-specific promoters have been reported for storage sink tissues such as seeds, potato tubers, and fruits (Edwards & Coruzzi, 1990), and for metabolic sink tissues such as meristems (Ito et al., 1994).

LITERATURE CITED

Akama et al., (1992). Plant Cell Reports 12: 7–11.

Baldi, B. G., Scott, J. J., Everard, J. D., and Loewus, F. A. (1988). Localization of constitutive phytases in lily pollen and properties of the pH 8 form. Plant Science 56, 137–147.

Barrientos, L., Scott, J. J., and Murthy, P. P. N. (1994). Specificity of hydrolysis of phytic acid by alkaline phytase from lily pollen. Plant Physiol. 106, 1489–1495.

Bateman, A., Birney, E., Durbin, R., Eddy, S. R., Finn, R. D., and Sonnhammer, E. L. L. (1999). Pfam 3.1: 1313 multiple alignments match the majority of proteins. Nucleic Acids Res., 27, 260–262.

Christou (1992). Plant J. 2: 275–281.

Crossway et al. (1986). Mol. gen. Genet. 202. 79–85.

Deblaere et al. (1985). Nucleic Acids Res. 13: 4777–4788.

Dvorakova, J. (1998). Phytase: sources, preparation and exploitation. Folia Microbiol. 43, 323–338.

Edwards & Coruzzi (1990). Annu. Rev. Genet. 24: 275–303.

Ehrlich, K. C., Montalbano, B. G., Mullaney, E. J., Dischinger, H. C., and Ullah, A. H. J. (1993). Identification and cloning of a second phytase gene (phyB) from *Aspergillus niger* (*ficuum*). Biochem. Biophys. Res. Commun. 195, 53–57.

Eeckhout, W. and Depaepe, M. (1994). Total phosphorus, phytate-phosphorus and phytase activity in plant feedstuffs. Anim. Feed Sci. Techn. 47, 19–29.

Engelen, A. J., Vanderheeft, F. C., Randsdorp, P. H. G., and Smit, E. L. C. (1994). Simple and rapid determination of phytase activity. Journal of AOAC International 77, 760–764.

Franck et al. (1980) Cell 21: 285–294.

Gasser et al (1993) Science, 244.

Gibson, D. M. and Ullah, A. H. J. (1988). Purification and characterization of phytase from cotyledons of germinating soybean seeds. Arch. Biochem. Biophys. 260, 503–513.

Gibson, D. M. and Ullah, A. H. J. (1990). Phytases and their action on phytic acid. In Inositol metabolism in plants. D. J. Morré, W. F. Boss, and F. A. Loewus, eds. (New York: Wiley-Liss), pp. 77–92.

Gram, N. H. (1982). The ultrastructure of germinating barley seeds I & II. Carlsberg Res. Commun. 47, 143–162.

Hofmann, K., Bucher, P., Falquet, L., and Bairoch, A. (1999). The PROSITE database, its status in 1999. Nucleic Acids Res., 27, 215–219.

Hoykas & Schilperoort (1992) Plant. Mol. Biol. 19: 15–38.

Irving, G. C. J. (1980). Intermediates in the dephosphorylation of P6-inositols by phytase enzymes. In Inositol phosphates: Their chemistry, biochemistry and physiology. D. J. Cosgrove, ed. (Amsterdam: Elsevier Scientific Publishing Company), pp. 99–117.

Ito et al. (1994) Plant. Mol. Bio. 24: 863–878.

Jia, Z., Golovan, S., Ye, Q., and Forsberg, C. W. (1998). Purification, crystallization and preliminiary X-ray analysis of the *Escherichia coli* phytas . Acta Cryst. 54, 647–649.

Johansen, K. S., Hatzack, F., Højrup, P., and Rasmussen, S. K. (2000). Purification and cloning of a wheat bran phytase (in prep.)

Johansen, K. S., Hatzack, F., Svendsen, I., Højrup, P., and Rasmussen, S. K. (2000). Purification and classification of a wheat bran phytase (in prep.).

Joshi & Joshi (1991) FEBS Left. 281: 1–8.

Kerovuo, J., Lauraeus, M., Nurminen, P., Kalkkinen, N., and Apajalahti, J. (1998). Isolation, characterization, molecular gene cloning, and sequencing of a novel phytase from *Bacillus subtilis*. Microbiology 64, 2079–2085.

Kerovuo, J, Rouvinen, R and F. Hatzack: Analysis of myo-inositol hexakisphosphate hydrolysis by *Bacillus* phytase: indication of a novel reaction mechanism. Biochem. J. (2000) 352, 623–628.

Kim, Y.-O., Lee, J.-H., Kim, H.-J., Yu, J.-H., and Oh, T.-K. (1998). Cloning of the thermostable phytase gene (phy) from *Bacillus* DS11 and its overexpression in *Escherichia coli*. Fems Microbiol. 162, 185–191.

Klee et al. (1987) Annu. Rev. Plant Physiol. 38: 467–486.

Kyhse-Andersen, J. (1984). Electroblotting of multible gels: A simple apparatus without buffertank for rapid transfer of proteins from polyacrylamide to nitrocellulose. J. Biochem. Biophys. Methods 10, 203–209.

Laboure, A., Gagnon, J., and Lescure, A. (1993). Purification and characterization of a phytase (myo-inositol-hexakisphosphate phosphohydrolase) accumulated in maize (*Zea mays*) seedlings during germination. Biochem. J. 295, 413–419.

Larsson, O., Barker, C. J., Sjoholm, Å., Carlqvist, H., Michell, R. H., Bertorello, A., Nilsson, T., Honkanen, R. E., Mayr, G. W., Zwiller, J., and Berggren, P. O. (1997). Inhibition of phosphatases and increased Ca2+ channel activity by inositol hexakisphosphate. Science 278, 471–474.

Lee, W. J. (1990). Phytic acid content and phytase activity of barley malt. ASBC J. 62–65.

Lim, P. E. and Tate, M. E. (1971). The phytases I. Lysolecithin activated phytase from wheat bran. Biochim. Biophys. Acta 250, 155–164.

Lim, P. E. and Tate, M. E. (1973). The phytases II. Properties of phytase fractions $F_1$ and $F_2$ from wheat bran and the myo-inositol phosphates produced by fraction $F_2$. Biochim. Biophys. Acta 302, 316–328.

Loewus, F. A. and Murthy, P. P. N. (2000). myo-Inositol metabolism in plants. Plant Science 150, 1–19.

Maugenest, S., Martinez, I., Godin, B., Perez, P., and Lescure, A. M. (1999). Structure of two maize phytase genes and their spatio-temporal expression during seedling development. Plant Mol. Biol. 39, 503–514.

Mitchell, D. B., Vogel, K., Weismann, B. J., Pasamontes, L., and van Loon, A. P. (1997). The phytase subfamily of histidine acid phosphatases: isolation of genes for two novel phytases from the fungi *Aspergillus terreus* and *Myceiophtora thermophila*. Microbiology 143, 245–252.

Muir, S. R. and Sanders, D. (1997). Inositol 1,4,5-trisphosphate-sensitive $Ca^{2+}$ release across nonvacuolar membranes in cauliflower. Plant Physiol. 114, 1511–1521.

Munnik, T., Irvine, R. F., and Musgrave, A. (1998). Phospholipid signalling in plants. Biochim. Biophys. Acta 1389, 222–272.

Nagai, Y. and Funahashi, S. (1962). Phytase (myo-inositolhexaphosphate phosphohydrolase) from wheat bran. Part I purification and substrate specificity. Agr. Biol. Chem. 26, 794–803.

Nagai, Y. and Funahashi, S. (1963). Phytase from wheat bran. Part II. Successive dephosphorylation of myo-inositolhexaphosphate by wheat bran phytase. Agr. Biol. Chem. 27, 619–624.

Nakano, T. et al., (1997). Purification and charact rization of phytase isoenzymes from wheat bran. Niigata daigaku nogakuba hokoku, Vol. 49, No. 2, 119–128.

Nakano, T. et al., (1999). Purification and characterization of phytase from Bran of *Triticum aestivum* L.cv. Food Sci. Technol. Res. 5(1), 18–23.

Nielsen, H., Engelbrecht, J., Brunak, S., and von Heijne, G. (1997). Identification of prokaryotic and eukaryotic signal peptides and prediction of their cleavage sites. Protein Engineering, 10, 1–6.

Nishino, H., Murakoshi, M., Masuda, M., Tokuda, H., Satomi, Y., Onozukam, M., Yamaguchi, S., Bu, P., Tsuruta, A., Nosaka, K., Baba, M., and Takasuka, N. (1999). Supression of lung and liver carcinogenesis in mice by oral administration of myo-inositol. Anticancer Res. 19, 3663–3664.

Pasamontes, L., Haiker, M., Wyss, M., Tessier, M., and Van Loon, A. P. G. M. (1997). Gene cloning, purifcation, and characterization of a heat-stable phytase from the fungus *Aspergillus fumigatus*. Applied and Environmental Microbiology 63, 1696–1700.

Pietrzak et al. (1986) Nucleic Acids Res. 14: 5857–5868.

Piddington, C. S., Houston, C. S., Paloheimo, M., Cantrell, M., Oinonen, A. M., Nevalainen, H., and Rambosek, J. (1993). The cloning and sequencing of the genes encoding phytase (phy) and pH 2.5-optimum acid phosphatase (aph) from *Aspergillus niger var. awarmori*. Gene 133, 55–62.

Potrykus, I., (1990) Bio/Tech., 8 p 535.

Potrykus, I., (1991) Annu. Rev. Plant Physiol. Plant Mol. Biol. 42: 205–225

Rasmussen, S. K. and Hatzack, F. (1998). Identification of two low-phytate barley (*Hordeum vulgare* L.) grain mutans by TLC and genetic analysis. Hereditas 129, 107–112.

Scott, J. J. and Loewus, F. A. (1986). A calcium-activated phytase from pollen of *Lilium longiflorum*. Plant Physiol. 82, 333–335.

Shamsuddin, A. M. and Vucenik, I. (1999). Mammary tumor inhibition by $IP_6$. A review. Anticancer Res. 19, 3671–3674.

Sharp, P. J., Kreis, M., Sh wry, P. R., and Gale, M. D. (1988). Location of beta-amylase sequences in wheat and its relatives. Theoretical and Applied Genetics, 75, 286–290.

Shimoto et al. (1989) Nature, 338, 274.

Stitt & Sonnewald (1995) Annu. Rev. Plant Physiol. Plant Mol. Biol. 46: 341–368.

Tague et al. (1988) Plant Phys. 86, p. 506.

Ullah, A. H. J. and Dischinger, H. C. (1993). *Aspergillus-Ficuum* Phytase—Complete Primary Structure Elucidation by Chemical Sequencing. Biochemical and Biophysical Research Communications 192, 747–753.

Ullah, A. H. J. and Gibson, D. M. (1987). Extracellular phytase (E.C. 3.1.3.8) from *Aspergillus ficuum* NRRL 3135: purification and characterization. Prep. Biochem. 17, 63–91.

Ullah, A. H. J. and Sethumadhavan, K. (1998). Differences in the active site environment of *Aspergillus ficuum* phytases. Biochem. Biophys. Res. Commun. 243, 458–462.

Ullah, A. H. J., Sethumadhavan, K., Mullaney, E. J., Ziegelhoffer, T., and Austin-Philps, S. (1999). Characterization of recombinant fungal phytase (phyA) expressed in tobacco leaves. Biochem. Biophys. Res. Commun. 264, 201–206.

van Hartingsveldt, W., van Zeijl, C. M. J., Harteveld, G. M., Gouka, R. J., Suykerbuyk, M. E. G., Luiten, R. G. M., van Paridon, P. A., Selten, G. C. M., Veenstra, A. E., van Gorcom, R. F. M., and van den Hondel, C. A. M. J. J.

(1993). Cloning, characterization and overexpression of phytase-encoding gene (phyA) of *Aspergillus niger*. Gene 127, 87–94.

York, J. D., Odom, A. R., Murphy, R., and Wente, S. R. (1999). A phospholipase C-dependent inositol polyphosphate kinase pathway required for efficient messenger RNA export. Science 285, 96–100.

Yoshida, T., Tanaka, K., and Kasai, Z. (1975). Phytase activity associated with isolated aleurone particles of rice grains. Agr. Biol. Chem. 39, 289–290.

Zhang, Z.-Y., Wang, Y., Wu, L., Fauman, E. B., Stuckey, J. A., Schubert, H. L., Saper, M. A., and Dixon, J. E. (1994). The Cys(x)$_5$Arg catalytic motif in phosphoester hydrolysis. Biochemistry 33, 15266–15270.

Zupan & Zambryski (1995) Plant Physiol. 107: 1041–1047.

EXAMPLE 1

The following is an example of the purification and production of a wheat bran phytase (SEQ ID NO: 7, which is encoded by SEQ ID NO: 8) according to the invention.

Materials

All reagents used were laboratory grade, all water used filtered through Millipore system. Havnemøllen (Århus) provided commercially available wheat bran.

Purification of Wheat Bran Phytase

Extraction of phytase activity from 2 kg wheat bran was performed using 10 l H$_2$O, 200 g PVPP and 5 mM β-mercaptoethanol. The suspension was stirred for 30 min. at room temperature and then filtrated through a fine mesh. The filtrate was adjusted to 50 mM NaAc pH 4.5 (buffer A) and centrifuged for 20 min at 8.000 rpm in a GSA rotor at 4° C. in a Sorwall centrifuge, to precipitate starch and insoluble protein. The supernatant was adjusted to 30% ammonium sulphate and incubated for 2 hours prior to centrifugation for 20 min at 8.000 rpm in a GSA rotor at 4° C. The resulting supernatant was adjusted to 60% ammonium sulphate, incubated and spun again. The pellet was solubilised in 200 ml buffer A and dialysed twice towards buffer A. The dialysed proteins were then diluted to 1 l with buffer A and loaded on a 600 ml SP sepharose (Pharmacia) column that was equilibrated in the same buffer. Bound proteins were eluted with 6 l of a linear gradient of 50 mM NaAc, 1M NaCl, pH 4.5 (buffer B). The resulting fractions were assayed for phytase activity using the assay of Engelen et al (Engelen et al., 1994) (adapted for eppendorf tubes). Fractions containing phytase activity were pooled, the protein precipitated by the addition of ammonium sulphate, the pellet resuspended and the buffer exchanged using HiTrap desalting columns (Pharmacia) to an unbuffered 1 mM NaCl solution. The resulting 50 ml extract was loaded on a 100 ml Ultrogel (hydroxy apatite, Sigma) column and the phytase activity was collected in the flow-through and initial wash. The phytase containing fraction was immediately adjusted to 50 mM NaAc pH 4.5 and 10% glycerol. The phytase-pool was then fractionated on a 6 ml Resource S column (Pharmacia) by elution with a linear gradient of buffer B. The procedure was repeated on a 1 ml Resource S column (Pharmacia). The phytase containing fractions were pooled and concentrated on Centricon 10 (Amicon) filters, loaded in 200 µl portions on a Superose gelfiltration column (Pharmacia) and collected in 300 µl fractions.

TABLE 1

An example of the purification of phytase from wheat bran

| Step | Volume (ml) | Enzyme activity (µmolP/min) | Protein (mg) | Specific Activity (µmolP/min/mg) | Purification fold | Yield % |
|---|---|---|---|---|---|---|
| Sample ready for SP-sepharose | 1000 | 3500 | 2230 | 1.57 | 1 | 100 |
| SP-sepharose | 650 | 2652 | 674 | 3.94 | 2.5 | 76 |
| SP-sepharose | 80 | 1375 | 573 | 2.40 | 1.5 | 39 |
| 60% (NH$_4$)$_2$SO$_4$+ buffer change | 180 | 530 | 119 | 4.46 | 2.8 | 24 |
| | 43 | 151 | 27.3 | 5.51 | 3.5 | 7 |
| Ultrogel Ressource S Gel filtration | 8 | 52 | 0.38 | 136.80 | 87.1 | 2 |

SDS-PAGE Analysis

After assaying for phytase activity the proteins in 100 µl of each fraction from the gelfiltration step were precipitated with methaNOl and chloroform (Wessel and Flügge, 1984) and subjected to SDS-PAGE using 4–12% Nupage gradient gels (NOVEX) and a Mes buffer pH 7.4. The gel was electrophoresed according to the manufactures manual with M12 (NOVEX) as molecular weight standard. Proteins were detected by silverstaining carried out as follows. The gel was soaked in 50% methanol, 10% acetic acid for 1 hour and rinsed in water 5 times during 1 hour. It was then incubated in 5 µg/ml dithiothreitol (DTT) for 30 min., rinsed quickly with water and soaked in 0.1% aqueous methanol for 1 hour. The gel was then rinsed once with water and once with 3% Na$_2$CO$_3$ before soaking in developer (100 ml 3% Na$_2$CO$_3$ containing 25 µl 37% formaldehyde). The reaction was stopped by the addition of 6 g citric acid.

Molecular Weight Determination

A superose (Pharmacia) gelfiltration column was equilibrated in 100 mM NaAc, 300 mM Nacl pH 5.5 and the elution time for the molecular weight standards IgG, Albumin, carbonic anhydrase, cytochrome C and Vitamin B12 (all from Pharmacia) determined. The concentrated semi-purified phytase was loaded in 200 µl portions and the eluent was collected in 200 µl fractions.

Determination of pH Optimum

Substrate solutions containing 5 mM phytate were prepared at different pH (4.0, 4.6, 5.0, 5.5, 6.0 NaAc; 6.0, 6.5, 7.0 Bis-Tris; 6.8, 7.6, 8.1 Tes buffer), and incubated with the purified wheat bran phytase for 30 min at 37° C.

Determination of Temperature Optimum

Figure 4:
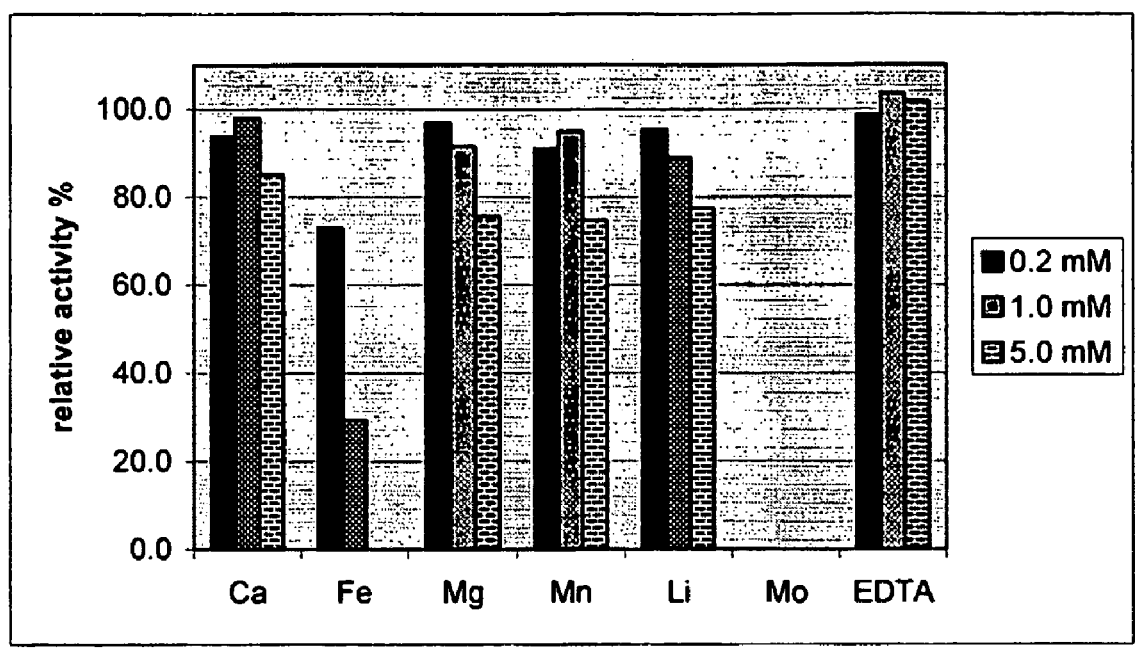
FIG. 4: the effect of various ions on the activity of the highly purified wheat bran phytase. Activities measured in the absence of additions to the reaction mix were set to 100%. The values are averages of two measurements.
Figure 5:
FIG. 5: depicts the isoelectric focusing of the purified wheat bran phytase. A double band at pH 7.4 is visible after incubation with 1-naphtylphosphate and Farst Garnet GBC.

The assay was carried out at 25, 37, 45, 50, 55, and 60° C., with the assay described above by incubating for 30 min at the indicated temperature Lineweaver-Burk plot was made from the results of incubating the wheat bran phytate substrate solutions of descending concentrations that were prepared in 50 mM NaAc. Substrate solutions with the following concentrations 5; 1.667; 1; 0.714; 0.556; 0.385; 0.294 mM were made and pH adjusted to 5.5. Wheat bran phytase has a broad temperature optimum (see FIG. 4). The reactions were incubated in a thermoblock at the indicated temp rature for 30 min. The highest value of activity (reached at 45° C.) was set to 100%.

Determination of the Effect of Divalent Cation on Phytase Activity

This was investigated by the addition of $CaCl_2$, $FeSO_4$, $MgCl$, $MnSO_4$, $LiCl$, $(NH_4)_6Mo_7O_{24}$, to the assay mixture. The final concentration used was 0.2, 1 and 5 mM. Gelfiltrated sample 5 μl (20 ng phytase) was added to each tube before incubating for 30 min at 37° C.

Determination of the Isoelectric Point

Proteins were focused at 11° C. for a total of 2.5 kVh in non-denaturing isoelectric-focusing polyacrylamid gels (IEF)(Ampholine PAGplate pH 3.5–9.5 (Pharmacia)). An IEF calibration kit (Pharmacia) was applied to determine the pH-gradient across the gel. The IEF markers were visualised by Coomassie staining according to the recommendations of the manufacturer. The presence of acid phosphatase was identified by incubation of the gel at 37° C. in 100 ml 0.05M citrate, pH 4.5 with 50 mg Na-1-naphtyl phosphate (Merck 6815), 25 mg Farst Garnet GBC (Sigma F-8761) and 0.5 ml 10% MgCl.

MDD-HPLC analyses of the degradation products: The substrate solution (Engelen et al., 1994) was diluted 1:10 and 20 μl used for assays with 2 μl enzyme and 8 μl 100 mM NaAc, pH 5.5. The reaction mixture was either stopped immediately or incubated 10 min at 37° C. The samples were analysed by the HPLC based metal dye-detection method as described previously (Mayr, 1990).

Amino Acid Sequencing

For amino acid sequencing, phytase containing sample was precipitated with methanol and chloroform prior to SDS-PAGE with Nupage gel as described above. Proteins were electroblotted onto 0.45 μm PVDF membrane (polyvinylidene diflouride) (Millipore) using a semidry blotting system (Kyhse-Andersen, 1984) (Hoefer Semiphor, Pharmacia).

The membrane was stained with coomassie blue for 30 seconds to visualise the proteins. Two bands corresponding to a molecular mass of ~56 kD were xcised and the proteins subjected to Edman degradation and the N-terminal sequence was determined.

Highly purified phytase fraction as shown in FIG. 1 lane 3 was sucked onto a filter and cleaved with CNBr in order to obtain internal amino acid sequence. The products were loaded onto the sequencer without prior separation.

Specificity of Phytase Antibody

Synthetic peptides corresponding to a 12 N-terminal amino acid sequence of the purified phytase enzyme (see: SEQ ID NO.:7) were conjugated to the carrier protein Keyhole limpet hemocyanin (synthesis and conjugation, K. J. Ross-Petersen, Hørsholm) and was used to raise antibodies in a rabbit. The serum from third bleed was tested in western blots.

Western Blot

SDS-PAGE and electroblotting of wheat bran protein samples was performed and the PVDF membrane was blocked with 2% Tween 20 in TBS (1xTBS: 6.06 g Tris; 8.77 g NaCl; pr. litre pH adjusted to 7.4 with HCl.) for 10 min. The membrane was washed in TBS and incubated in 0.5% Tween 20 in TBS with 1:500 V/V serum containing the wheat bran phytase antibody for one hour. The membrane was washed three times 5 min in TBS and incubated with 1:2000 swine-anti-rabbit alkaline phosphatase conjugated secondary antibodies (DAKO, Denmark) for 1 hour. Incubations were performed at room temperature in sealed plastic bags. The membrane was then three times 5 min. in TBS before staining in 20 ml freshly made 0.1 M ethanolamine pH 9.6, with 1.2 mg 5-bromo-4-choro-3-indoyl phosphate (BCIP), 3 mg nitroblue tetrazolium (NBT) and 80 μl M MgCl. The developed blot was washed in water and dried.

MALDI MS Sample Preparation and Analysis:

Gel slices containing the ~56 and ~66 kD protein, as shown in FIG. 1B, were excised from the NuPage gel, transferred to separate eppendorf tube and cut in 1 mm² pieces. The gel particles were washed with water and 0.1 M $NH_4HCO_3$/acetonitrile 1:1 (v/v), all remaining liquid removed and acetonitrile added to cover the gel particles. Acetonitrile was removed and the gel particles rehydrated in 0.1 M $NH_4HCO_3$. After 5 minutes, an equal volume of acetonitrile was added and the pieces incubated for 15 min. The liquid was removed and gel particles dried down in a vacuum centrifuge.

The protein was reduced and alkylated by first swelling the gel particles in 10 mM dithiotreitol/0.1 M $NH_4HCO_3$ and incubating for 45 min at 56° C. After chilling to room temperature the liquid was quickly replaced with roughly the same volume of freshly prepared 55 mM iodoacetamide in 0.1 M $NH_4HCO_3$. The protein containing gel particles were incubated for 30 minutes at room temperature in the dark. Iodoacetamide solution was removed, and the gel particles washed with 0.1 M $NH_4HCO_3$ and acetonitrile as described above.

Gel particles were completely dried down in a speed vac, and subsequently rehydrated in a freshly prepared and chilled digestion buffer containing 50 mM $NH_4HCO_3$, 5 mM CaCl2 and 12.5 ng/μL of trypsin (Promega, modified, sequencing grade) at 4° C. The remaining supernatant was, after 45 min, replaced with 5–20 μL of the same buffer without trypsin. The digestion reaction was incubated at 37° C. overnight.

The peptides were extracted from the gel with acetonitrile containing 25 mM $NH_4HCO_3$, and then dried in a vacuum centrifuge. The peptides were re-dissolved in 10 μl 5% formic acid and 0.5 μl analysed by MALDI MS using the dried droplet method.

Immuno-chemistry

Figure 6:
FIG. 6: westernblot analysis of wheat bran proteins on PVDF membrane. The membrane was cut in two after the transfer proteins: lanes 1, 2, and 3 were coomassie blue stained, lanes 4, 5, and 6 were incubated with primary antibodies against the N-terminal of the phytase polypeptide and alkaline phosphatase conjugated secondary antibodies. Loading: lane 1, M12 MW markers (kD indicated to the left); lanes 2, 250 ng and 4, 125 ng purified phytase; lanes 3 and 5, 2 µl semi-purified preparation; lane 6, SeeBlue MW markers. The arrow indicates the position of the phytase bands.

A synthetic peptide conjugated to a carrier protein was used to raise antibodies in rabbit. As can be seen in FIG. 6, the polyclonal antibodies clearly mark the 66 kD peptide band at very low concentrations in both the highly purified and in a semi-purified wheat bran extract. The 25 kD band visible in lane 5 is due to unspecific interactions with the major impurity (clearly visible in the coomassie stained lane 3) in this fraction. Westernblot: SDS-PAGE and electroblotting of wheat bran protein samples was performed and the PVDF membran was blocked with 2% Tween 20 in TBS (1xTBS: 6.06 g Tris; 8.77 g NaCl; pr. litre pH adjusted to 7.4 with HCl.) for 10 min. The membrane was washed in TBS and incubated in 0.5% Tween 20 in TBS with 1:500 V/V serum containing the wheat bran phytase antibody for one hour. The membrane was washed three times 5 min in TBS and incubated with 1:2000 swine-anti-rabbit alkaline phosphatase conjugated secondary antibodies (DAKO, Denmark) for 1 hour. Incubations were performed at room temperature in sealed plastic bags. The membrane was then three times 5 min. in TBS before staining in 20 ml freshly made 0.1 M ethanolamine pH 9.6, with 1.2 mg 5-bromo-4-choro-3-indoyl phosphate (BCIP), 3 mg nitroblue tetrazolium (NBT) and 80 μl M MgCl. The developed blot was washed in water and dried.

Cloning

The following is an example of cloning and sequencing procedures for identification of nucleotide sequences encoding phytase enzymes from wheat and barley:

PCR Primers and Oligonucleotides

The following oligonucleotides were used in the isolation of the wheat phytase gene and cDNA:

| Name | Sequence | |
|---|---|---|
| INT F1 V1 | TAYCCIGGICGIATIGCIGTIGTIGGIGA | (SEQ ID NO:14) |
| INT F1 V2 | TAYCCIGGIAGRATIGCIGTIGTIGGIGA | (SEQ ID NO:15) |
| HVR1 | GAGCGCTCGTACGCGTGCACATGGCC | (SEQ ID NO:16) |
| HVR2 | TTCCCGCCGTCGCCCACCGAGAT | (SEQ ID NO:17) |
| HVR3 | GGGCAGTGCCCCGGCTCGTCGGC | (SEQ ID NO:18) |
| HVR4 | GAGATGTACACGGCGCCGCA | (SEQ ID NO:19) |
| HVR5 | GGTCCTGGTTCCTGTGCCATC | (SEQ ID NO:20) |
| PH-W-1 | ACGTCTTGTTGCCGATCTGCTCCTC | (SEQ ID NO:21) |
| PH-W-2 | AGGAGCAGGAGTAGCAGTCCGTTCC | (SEQ ID NO:22) |
| PH-W-3 | GAGGTGGTGTTGTACGTGAG | (SEQ ID NO:23) |
| Ad1 | GTAATACGACTCACTATAGGGCACGCGTGGTCGACGGCCCGGGCTGGT | (SEQ ID NO:24) |
| Ad2 | ACCAGCCC | (SEQ ID NO:25) |
| AP1 | GTAATACGACTCACTATAGGGC | (SEQ ID NO:26) |
| AP2 | ACTATAGGGCACGCGTGGT | (SEQ ID NO:27) |
| PH-W2-1 | AAAGAATCGGCGGCGAGCCCGTAGCG | (SEQ ID NO:28) |
| PH-W2-2 | CGTGCCGGGGTCCAGCGGCTTGACGG | (SEQ ID NO:29) |
| PH-W2-3 | ACGGTGCCGCCCATCTGG | (SEQ ID NO:30) |
| PH-RT-F | ACGTACAACACCACCTCGACCG | (SEQ ID NO:31) |
| PH-RT-R | CGGGTCCAGCGTGTAGTTGAAC | (SEQ ID NO:32) |
| PH-cDNA-F2 | ACACTCACCTCGCACTGCTCTC | (SEQ ID NO:33) |
| PH-cDNA-R | TTACGGACCGTGTGCGGGCCTGGTCCAGTT | (SEQ ID NO:34) |

Purification of DNA and RNA

Chromosomal DNA (gDNA) was isolated from leaf material from young seedlings of wheat (cv. Kadett) or barley (cv. Alexis) by homogenisation in liquid $N_2$ followed by several phenol/chloroform extractions and ethanol precipitation (Sharp et al., 1988). Total RNA was isolated from developing wheat kernels harvested approximately 20 days after anthesis using TRIzol reagent (Life Technologies) according to the manufacturers instructions.

Cloning and Sequencing

PCR products were cloned into the pCR4-TOPO vector using "TOPO TA Cloning Kit for Sequencing" (Invitrogen) according to the manufacturers instructions. Sequencing reactions with T3, T7 or gene insert specific primers were performed using the DYEnamic ET sequencing kit (Amersham Pharmacia Biotech) according to instructions, separated on a Perkin Elmer ABI Prism 377 automated sequencer and analysed using the accompanying software, Sequencher v3.1.1 (Gene Codes Corporation) and MacVector v7.0 (Oxford Molecular) software packages. A minimum of three independent clones of each PCR product were sequenced to resolve PCR based mis-incorporations.

Genomic PCR Using Degenerate Primers

PCR reactions (50 mM KCl; 10 mM Tris-HCl, pH 9.0; 0.1% Triton X-100; 1.25 mM $MgCl_2$; 0.2 mM dNTPs; 0.2 u Taq polymerase) with 100 ng wheat gDNA, 20 pmol of a 1:1 mix of two degenerate forward primers (INT F1 V1, INT F1 V2) corresponding to the reverse translation of the internal phytase peptide (YPGRIAVVGD (SEQ ID NO: 35)) and 5 pmol of a reverse primer derived from the barley EST clone BE602374 (HVR1, HVR2, HVR3, HVR4 or HVR5) with the following parameters: 35×(95° C., 0 m 45 s; 60° C. 1 m 00; 72° C. 2 m 30 s). The PCR product obtained with the HVR3 reverse primer were re-amplified using 1/40 of the original PCR reaction as template, the same forward primer and the internal HVR2 reverse primer, confirming that it represented a phytase sequence. The re-amplification product was gel-purified using the Geneclean Spin Kit (BIO101), cloned and sequenced. The resulting sequence covers 728 bp of coding sequence interrupted by two introns of approximately 100 bp each, at conserved positions relative to the introns in the putative purple acid phosphatase from *Arabidopsis* (AAF20233).

Genomic Walk PCR

To identify the 5' end of the wheat phytase gene, genomic walk libraries were prepared by digestion of wheat gDNA with a restriction enzyme giving blunt-ended fragments (EcoRV, DraI, PvuII or HindII) followed by ligation of an asymmetric adapter (Ad1+Ad2) in which Taq polymerase extension of the short lower strand is blocked by an amino-modification of the 3' end. Primary PCR reactions were performed using walk library corresponding to 6.25 ng gDNA as template and the first adapter primer (AP1) in combination with PH-W-1 (annealing 300 bp from the 5' end of the sequence obtained by degenerate PCR) using polymerase mix and reagents from the "Expand Long Template PCR kit" (Boehringer Mannheim) and the following parameters: 7×(94° C. 0 m 45 s, 72° C. 3 m 30 s)+32×(94° C. 0 m 45 s, 67° C. 3 m 30 s). Secondary nested PCR reactions were performed under identical conditions and cycling parameters using the nested adapter primer (AP2), PH-W-2 (annealing 151 bp upstream of PH-W-1) and 1/40 of the primary PCR reaction as template. A tertiary PCR reaction was performed using AP2, PH-W-3 (annealing 263 bp upstream of PH-W-1) and 1/40 of the secondary PCR reaction as template with parameters: 25×(94° C. 0 m 45 s, 50° C. 0 m 45 s, 72° C. 2 m 30 s). A specific PCR product amplified from the HindII library was isolated, cloned and sequenced. Although this extended the phytase coding sequence with 322 bp upstream of the 5' end of the degenerate PCR product, covering a 97 bp intron again at a conserved position, the amino-terminal peptide sequence was not included on this fragment. New walk primers (PH-W2-1, PH-W2-2, PH-W2-3) were constructed based on the additional sequence information and identical nested PCR reactions were repeated on the original walk libraries. Cloning and sequencing of a 541 bp fragment amplified from the PvuII library revealed that it covered a fourth conserved intron, the amino terminal peptide sequence and included the 5' end of the coding sequence.

RT-PCR

Primers for RT-PCR amplification of the wheat phytase coding sequence (PH-cDNA-F2, PH-RT-F, PH-RT-R and PH-cDNA-R) were designed from the identified genomic sequence. First strand cDNA synthesis was performed using total RNA from developing kernels using SuperscriptII (GIBCO-BRL) reverse transcriptase with either of the two reverse primers under the conditions described by the manufacturer. Amplification of the entire cDNA using the PH-cDNA-F2/PH-cDNA-R primer combination was not possible probably due to a very high G+C content (>80%) particularly in the first part of the coding region and the relatively large size of the product. Alternative the cDNA was isolated as two overlapping fragments using the primer combinations PH-cDNA-F2/PH-RT-R and PH-RT-F/PH-cDNA-R under the following conditions 95° C. 1 m 30 s, 35×(95° C. 0 m 30 s, 65° C. 0 m 45 s, 72° C. 2 m 00 s).

Characteristics of the Wheat Phytase cDNA Sequence

The wheat phytase cDNA sequence contains an open reading frame of 1620 nucleotides encoding a deduced amino acid sequence 540 amino acids.

The wheat phytase is predicted (using the signalP prediction method described by Nielsen et al., "Identification of Prokaryotic and Eukaryotic Signal Peptides and Prediction of Their Cleavage Sites," *Protein Engineering* 10:1–6, 1997) to contain a signal peptide targeting it for export through the endoplasmic reticulum, possibly with the vacuole as the final destination. The signal peptide cleavage site is predicted to be immediately preceding one of the four amino acids from position 19–22, which is in excellent agreement with the amino terminal sequence found in the purified enzyme. Assuming signal peptide cleavage after position 21 of the deduced amino acid sequence, the predicted molecular mass of the mature phytase polypeptide is 57.7 kDa in excellent correspondence with the estimated molecular mass of 56 kDa for the purified phytase enzyme. Analysis of the deduced protein sequence reveals the presence of 8 putative N-glycosylation sites. One or more of these sites might be used for modification of the protein during transport through the endoplasmic reticulum and golgi apparatus, resulting in the creation of a phytase population with heterogeneous mass. Thus, glycosylation might explain the detection of phytase activities of higher apparent molecular masses.

Scanning the deduced phytase sequence against the Prosite (Hofmann et al., 1999) and Pfam (Bateman et al., 1999) databases resulted in only one significant hit: the Pfam purple acid phosphatase profile, strongly suggesting that the wheat phytase belongs to this enzyme class. Additionally, alignment of the deduced wheat phytase sequence with kidney bean purple acid phosphatase (P80366) reveals that all seven metal-chelating and several neighbouring residues, which have been identified in the active site of the latter by X-ray crystallography are conserved in the wheat phytase.

Figure 7:
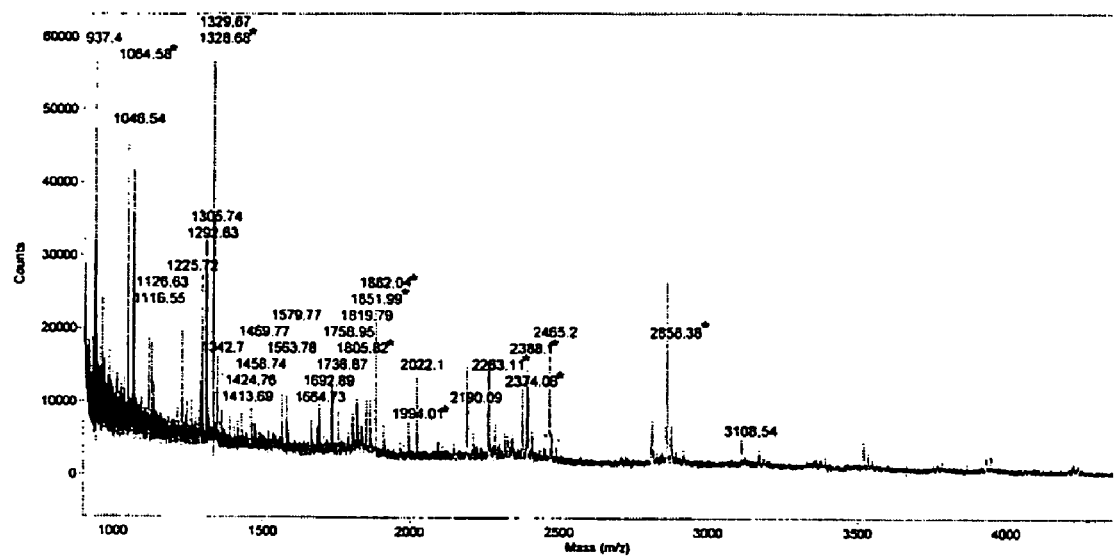
FIG. 7: shows the MALDI-TOF MS analysis of the tryptic fragments of the wheat bran phytase. MALDI-TOF MS analysis of the tryptic fragments of the wheat bran phytase. The peaks of 1046.54 and 2465.2 are internal standards. Peaks found in the fingerprint of both the 56 kD and the 66 kD bands are indicated by an * next to the mass.
Figure 9:
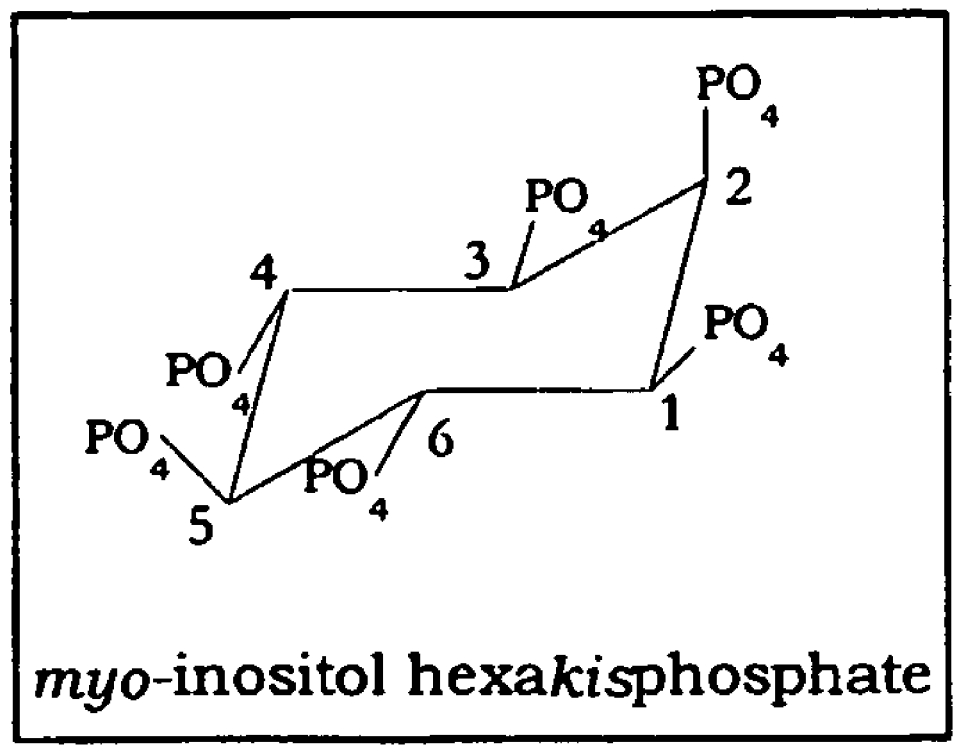
FIG. 9: shows the structure of phytate where the numbering is according to the D-configuration.

Seven of the tryptic fragments predicted from the deduced wheat phytase sequence correspond closely in molecular mass to fragments identified in MALDI-TOF MS analysis of trypsin treated purified wheat bran phytase (FIG. 7). The matched fragments, five of which are found in both the 56 and 66 kDa bands of the wheat bran phytase and two of which overlaps strongly conserved sites in purple acid phosphatase, are the following:

| Position | predicted MW | Observed MW |
| --- | --- | --- |
| 380–404 | 2859.07 | 2858.38 |
| 351–369 | 2263.48 | 2263.11 |
| 432–447 | 1734.79 | 1736.87 |
| 43–54 | 1292.30 | 1292.63 |
| 484–495 | 1302.35 | 1305.74 |
| 246–256 | 1328.39 | 1328.68 |
| 107–116 | 1064.14 | 1064.58 |

This confirms the relation between the purified wheat bran phytase and the cloned cDNA sequence. However, the presence of multiple unmatched fragments together with the three amino acid differences between the sequences identified by Edman degradation of the purified phytase and the sequence deduced from the cDNA strongly suggest that they represent products from two different genes. This is not unexpected considering that common domesticated wheat is hexaploid and thus probably harbouring phytase genes, that might have diverged, on each of the three constituent genomes.

The embodiments of the invention in which an exclusive property or privilege is claimed are defined as follows:

1. A DNA fragment comprising a sequence encoding a polypeptide capable of hydrolyzing the substrate phytate (1, 2, 3, 4, 5, 6, myo-inositol-hexakisphosphate, phytic acid), wherein the polypeptide has a sequence identity of at least 95% with SEQ ID NO: 7.

2. The DNA fragment of claim 1, wherein the DNA fragment is cDNA.

3. The cDNA fragment of claim 2, wherein the cDNA fragment encodes the polypeptide of SEQ ID NO: 7.

4. An expression cassette comprising the DNA fragment as defined in claim 1.

5. A cell which is capable of expressing a polypeptide and which is transformed with the expression cassette as defined in claim 4.

6. A method of producing a recombinant polypeptide capable of hydrolysing the substrate phytate (1,2,3,4,5,6 myo-inositol-hexakisphosphate, phytic acid), comprising culturing the cell as defined in claim 5, in a suitable culture medium under conditions allowing expression of the polypeptide, and recovering the polypeptide from the culture.

* * * * *

SEQUENCE LISTING

<160> NUMBER OF SEQ ID NOS: 12

<210> SEQ ID NO 1
<211> LENGTH: 15
<212> TYPE: PRT
<213> ORGANISM: Triticum aestivum

<400> SEQUENCE: 1

Glu Pro Ala Ser Thr Leu Thr Gly Pro Ser Arg Pro Val Thr Val
1               5                   10                  15

<210> SEQ ID NO 2
<211> LENGTH: 19
<212> TYPE: PRT
<213> ORGANISM: Triticum aestivum
<220> FEATURE:
<221> NAME/KEY: MISC_FEATURE
<222> LOCATION: (2)..(2)
<223> OTHER INFORMATION: Xaa = Any amino acid

<400> SEQUENCE: 2

Met Xaa Ala Val Gly Ser Asp Ser Tyr Pro Gly Arg Ile Ala Val Val
1               5                   10                  15

Gly Asp Leu

<210> SEQ ID NO 3
<211> LENGTH: 15
<212> TYPE: PRT
<213> ORGANISM: Triticum aestivum
<220> FEATURE:
<221> NAME/KEY: MISC_FEATURE
<222> LOCATION: (3)..(4)
<223> OTHER INFORMATION: Xaa = Any amino acid
<220> FEATURE:
<221> NAME/KEY: MISC_FEATURE
<222> LOCATION: (6)..(6)
<223> OTHER INFORMATION: Xaa = Any amino acid
<220> FEATURE:
<221> NAME/KEY: MISC_FEATURE
<222> LOCATION: (9)..(10)
<223> OTHER INFORMATION: Xaa = Any amino acid
<220> FEATURE:
<221> NAME/KEY: MISC_FEATURE
<222> LOCATION: (12)..(13)
<223> OTHER INFORMATION: Xaa = Any amino acid

<400> SEQUENCE: 3

Met Leu Xaa Xaa Tyr Xaa Asp Tyr Xaa Xaa Ser Xaa Xaa Gln Tyr
1               5                   10                  15

<210> SEQ ID NO 4
<211> LENGTH: 20
<212> TYPE: PRT
<213> ORGANISM: Triticum aestivum

<400> SEQUENCE: 4

Thr Met Ser Ala Asn Gly Ser Asp Ser Tyr Pro Gly Arg Ile Ala Val
1               5                   10                  15

Val Gly Asp Leu
            20

<210> SEQ ID NO 5
<211> LENGTH: 20
<212> TYPE: PRT
<213> ORGANISM: Triticum aestivum -continued

```
<400> SEQUENCE: 5

Thr Met Gly Ala Asn Gly Ser Asp Ser Tyr Pro Gly Arg Ile Ala Val
1               5                   10                  15

Val Gly Asp Leu
            20

<210> SEQ ID NO 6
<211> LENGTH: 12
<212> TYPE: PRT
<213> ORGANISM: Triticum aestivum

<400> SEQUENCE: 6

Glu Pro Ala Ser Thr Leu Thr Gly Pro Ser Arg Pro
1               5                   10

<210> SEQ ID NO 7
<211> LENGTH: 540
<212> TYPE: PRT
<213> ORGANISM: Triticum aestivum

<400> SEQUENCE: 7

Met Trp Met Trp Arg Gly Ser Leu Pro Leu Leu Leu Ala Ala Ala Ala
1               5                   10                  15

Val Ala Ala Ala Glu Pro Ala Ser Thr Leu Glu Gly Pro Ser Arg
                20                  25                  30

Pro Val Thr Val Pro Leu Arg Glu Asp Arg Gly His Ala Val Asp Leu
            35                  40                  45

Pro Asp Thr Asp Pro Arg Val Gln Arg Val Thr Gly Trp Ala Pro
        50                  55                  60

Glu Gln Ile Ala Val Ala Leu Ser Ala Ala Pro Thr Ser Ala Trp Val
65                  70                  75                  80

Ser Trp Ile Thr Gly Asp Phe Gln Met Gly Gly Ala Val Lys Pro Leu
                85                  90                  95

Asp Pro Gly Thr Val Gly Ser Val Val Arg Tyr Gly Leu Ala Ala Asp
            100                 105                 110

Ser Leu Val Arg Glu Ala Thr Gly Asp Ala Leu Val Tyr Ser Gln Leu
        115                 120                 125

Tyr Pro Phe Glu Gly Leu Gln Asn Tyr Thr Ser Gly Ile Ile His His
    130                 135                 140

Val Arg Leu Gln Gly Leu Glu Pro Gly Thr Lys Tyr Tyr Tyr Gln Cys
145                 150                 155                 160

Gly Asp Pro Ala Ile Pro Gly Ala Met Ser Ala Val His Ala Phe Arg
                165                 170                 175

Thr Met Pro Ala Val Gly Pro Arg Ser Tyr Pro Gly Arg Ile Ala Val
            180                 185                 190

Val Gly Asp Leu Gly Leu Thr Tyr Asn Thr Thr Ser Thr Val Asp His
        195                 200                 205

Met Ala Ser Asn Arg Pro Asp Leu Val Leu Leu Val Gly Asp Val Cys
    210                 215                 220

Tyr Ala Asn Met Tyr Leu Thr Asn Gly Thr Gly Ala Asp Cys Tyr Ser
225                 230                 235                 240

Cys Ala Phe Gly Lys Ser Thr Pro Ile His Glu Thr Tyr Gln Pro Arg
                245                 250                 255

Trp Asp Tyr Trp Gly Arg Tyr Met Glu Ala Val Thr Ser Gly Thr Pro
            260                 265                 270

Met Met Val Val Glu Gly Asn His Glu Ile Glu Glu Gln Ile Gly Asn
```

-continued

```
                275                 280                 285
Lys Thr Phe Ala Ala Tyr Arg Ser Arg Phe Ala Phe Pro Ser Thr Glu
            290                 295                 300
Ser Gly Ser Phe Ser Pro Phe Tyr Tyr Ser Phe Asp Ala Gly Gly Ile
305                 310                 315                 320
His Phe Leu Met Leu Gly Ala Tyr Ala Asp Tyr Gly Arg Ser Gly Glu
                325                 330                 335
Gln Tyr Arg Trp Leu Glu Lys Asp Leu Ala Lys Val Asp Arg Ser Val
            340                 345                 350
Thr Pro Trp Leu Val Ala Gly Trp His Ala Pro Trp Tyr Thr Thr Tyr
            355                 360                 365
Lys Ala His Tyr Arg Glu Val Glu Cys Met Arg Val Ala Met Glu Glu
        370                 375                 380
Leu Leu Tyr Ser His Gly Leu Asp Ile Ala Phe Thr Gly His Val His
385                 390                 395                 400
Ala Tyr Glu Arg Ser Asn Arg Val Phe Asn Tyr Thr Leu Asp Pro Cys
                405                 410                 415
Gly Ala Val His Ile Ser Val Gly Asp Gly Gly Asn Arg Glu Lys Met
            420                 425                 430
Ala Thr Thr His Ala Asp Glu Pro Gly His Cys Pro Asp Pro Arg Pro
            435                 440                 445
Lys Pro Asn Ala Phe Ile Gly Gly Phe Cys Ala Phe Asn Phe Thr Ser
        450                 455                 460
Gly Pro Ala Ala Gly Arg Phe Cys Trp Asp Arg Gln Pro Asp Tyr Ser
465                 470                 475                 480
Ala Tyr Arg Glu Ser Ser Phe Gly His Gly Ile Leu Glu Val Lys Asn
                485                 490                 495
Glu Thr His Ala Leu Trp Arg Trp His Arg Asn Gln Asp Met Tyr Gly
            500                 505                 510
Ser Ala Gly Asp Glu Ile Tyr Ile Val Arg Glu Pro His Arg Cys Leu
            515                 520                 525
His Lys His Asn Trp Thr Arg Pro Ala His Gly Pro
        530                 535                 540
```

<210> SEQ ID NO 8
<211> LENGTH: 1623
<212> TYPE: DNA
<213> ORGANISM: Triticum aestivum

<400> SEQUENCE: 8

```
atgtggatgt ggagggggtc gctgccgctg cttctgctcg ccgcggcggt ggcggcggcg    60
gctgagccgg cgtcgacgct ggagggaccg tcgcggccgg tgacggtgcc gctgcgggaa   120
gacaggggcc acgcggtgga cctgccggac acggaccccc gggtgcagcg ccgggtcaca   180
ggctgggctc ccgagcagat cgccgtcgcg ctctccgccg ctcccacctc cgcctgggtc   240
tcctggatca caggggattt ccagatgggc ggcgccgtca agccgctgga ccccggcacg   300
gtcggcagcg tcgtgcgcta cggcctcgcc gccgattctt tggtccgcga ggccaccggc   360
gacgcgctcg tgtacagcca gctctacccc ttcgagggcc tccagaacta cacctccggc   420
atcatccacc acgtccgcct ccaagggctt gagcctggga cgaagtacta ctaccagtgc   480
ggcgacccgg ccatcccggg ggcgatgagc gccgtccacg cgttccggac gatgccggcg   540
gtcgggccgc ggagctaccc ggggaggatc gccgtggtgg gggacctcgg gctcacgtac   600
aacaccacct cgaccgtgga ccacatggcg agcaaccggc cggacctggt cctcctcgtc   660
```

-continued

```
ggcgacgtgt gctacgccaa catgtacctc accaacggca ccggagcgga ctgctactcg      720
tgcgcgttcg gcaagtcgac gcccatccac gagacgtacc agccgcgctg ggactactgg      780
ggaaggtaca tggaggcggt gacgtcgggg acgccgatga tggtggtgga agggaaccat      840
gagatagagg agcagatcgg gaacaagacg ttcgcggcct accgctcccg gttcgcgttc      900
ccgtcgacgg agagcgggtc cttctccccc ttctactact cgttcgacgc cggcgggatc      960
catttcctca tgctcggcgc ctacgccgac tacggcaggt caggggagca gtacagatgg     1020
ctggagaagg acctggcgaa ggtggacagg tcggtgacgc cgtggctggt cgccggctgg     1080
cacgcgccat ggtacaccac ctacaaggct cactacaggg aggtggagtg catgagagtg     1140
gccatggagg agctgctcta ctcccacggc ctcgacatcg ccttcaccgg ccatgtgcac     1200
gcgtatgagc gctccaaccg ggtgttcaac tacacgctgg acccgtgcgg cgccgtgcac     1260
atctcggtgg cgacggcgg gaaccgcgag aagatggcca ccacccacgc cgacgagcca     1320
gggcactgcc cggacccgcg gcccaagccc aacgccttca tcggcggctt ctgcgccttt     1380
aacttcacgt ccggcccggc cgccggcagg ttctgctggg accggcagcc ggactacagc     1440
gcctaccggg agagcagctt cggccacggc atcctcgagg tgaagaacga gacgcacgct     1500
ctgtggagat ggcacaggaa ccaggacatg tacgggagcg ccggagatga gatttacatt     1560
gtccgggagc cgcacaggtg cttgcacaaa cacaactgga ccaggcccgc acacggtccg     1620
taa                                                                   1623
```

<210> SEQ ID NO 9
<211> LENGTH: 455
<212> TYPE: PRT
<213> ORGANISM: Hordeum vulgare

<400> SEQUENCE: 9

```
Glu Phe Gln Met Gly Gly Thr Val Lys Pro Leu Asp Pro Arg Thr Val
1               5                   10                  15

Gly Ser Val Val Arg Tyr Gly Leu Ala Ala Asp Ser Leu Val Arg Glu
            20                  25                  30

Ala Thr Gly Asp Ala Leu Val Tyr Ser Gln Leu Tyr Pro Phe Glu Gly
        35                  40                  45

Leu His Asn Tyr Thr Ser Gly Ile Ile His Val Arg Leu Gln Gly
    50                  55                  60

Leu Glu Pro Gly Thr Lys Tyr Tyr Tyr Gln Cys Gly Asp Pro Ala Ile
65                  70                  75                  80

Pro Gly Ala Met Ser Ala Val His Ala Phe Arg Thr Met Pro Ala Ala
                85                  90                  95

Gly Pro Arg Ser Tyr Pro Gly Arg Ile Ala Val Val Gly Asp Leu Gly
            100                 105                 110

Leu Thr Tyr Asn Thr Thr Ser Thr Val Asp His Met Thr Ser Asn Arg
        115                 120                 125

Pro Asp Leu Val Val Leu Val Gly Asp Val Ser Tyr Ala Asn Met Tyr
    130                 135                 140

Leu Thr Asn Gly Thr Gly Thr Asp Cys Tyr Ser Cys Ser Phe Gly Lys
145                 150                 155                 160

Ser Thr Pro Ile His Glu Thr Tyr Gln Pro Arg Trp Asp Tyr Trp Gly
                165                 170                 175

Arg Tyr Met Glu Pro Val Thr Ser Ser Thr Pro Met Met Val Val Glu
            180                 185                 190
```

-continued

Gly Asn His Glu Ile Glu Glu Gln Ile Gly Asn Lys Thr Phe Ala Ala
            195                 200                 205

Tyr Arg Ser Arg Phe Ala Phe Pro Ser Ala Glu Ser Gly Ser Phe Ser
        210                 215                 220

Pro Phe Tyr Tyr Ser Phe Asp Ala Gly Gly Ile His Phe Ile Met Leu
225                 230                 235                 240

Gly Ala Tyr Ala Asp Tyr Gly Arg Ser Gly Glu Gln Tyr Arg Trp Leu
                245                 250                 255

Glu Lys Asp Leu Ala Lys Val Asp Arg Ser Val Thr Pro Trp Leu Val
            260                 265                 270

Ala Gly Trp His Ala Pro Trp Tyr Ala Thr Tyr Lys Ala His Tyr Arg
        275                 280                 285

Glu Val Glu Cys Met Arg Val Ala Met Glu Glu Leu Leu Tyr Ser His
    290                 295                 300

Gly Leu Asp Ile Ala Phe Thr Gly His Val His Ala Tyr Glu Arg Ser
305                 310                 315                 320

Asn Arg Val Phe Asn Tyr Thr Leu Asp Pro Cys Gly Ala Val Tyr Ile
                325                 330                 335

Ser Val Gly Asp Gly Gly Asn Arg Glu Lys Met Ala Thr His Ala
            340                 345                 350

Asp Glu Pro Gly His Cys Pro Asp Pro Arg Pro Lys Pro Asn Ala Phe
        355                 360                 365

Ile Ala Gly Phe Cys Ala Phe Asn Phe Thr Ser Gly Pro Ala Ala Gly
370                 375                 380

Arg Phe Cys Trp Asp Arg Gln Pro Asp Tyr Ser Ala Tyr Arg Glu Ser
385                 390                 395                 400

Ser Phe Gly His Gly Ile Leu Glu Val Lys Asn Glu Thr His Ala Leu
                405                 410                 415

Trp Arg Trp His Arg Asn Gln Asp Leu Tyr Gly Ser Ala Gly Asp Glu
            420                 425                 430

Ile Tyr Ile Val Arg Glu Pro Glu Arg Cys Trp His Lys His Asn Trp
        435                 440                 445

Thr Arg Pro Ala His Gly Pro
    450                 455

<210> SEQ ID NO 10
<211> LENGTH: 1370
<212> TYPE: DNA
<213> ORGANISM: Hordeum vulgare

<400> SEQUENCE: 10
gggaattcca gatgggcggc accgtgaagc cgctggaccc ccgcacggtc ggcagcgtcg     60
tgcgctacgg gctcgccgcc gactcttggg ttcgcgaggc caccggcgac gcgctcgtgt    120
acagccagct ctacccttc gagggcctcc acaactacac ctccggcatc atccaccacg    180
tccgcctcca agggcttgag cctgggacca agtactacta ccagtgcggc gacccggcca    240
tcccgggggc gatgagcgcc gtccacgcgt tccggacgat gccggcggcg ggccgcgga    300 gctaccgggg gaggatcgcc gtggtgggag acctcgggct cacgtacaac accacctcga    360
ccgtggacca catgacgagc aaccggccgg acctggtcgt cctcgtcggc gacgtcagct    420
acgccaacat gtacctcacc aacggcaccg gaacggactg ctactcctgc tccttcggca    480
agtcaacgcc catccacgaa acctaccagc cgcgctggga ctactgggga aggtacatgg    540
agccggtgac gtcgagcacg ccgatgatgg tggtggaagg gaaccacgag atagaggagc    600

-continued

| | |
|---|---|
| agatcggcaa caagacgttc gcggcctacc gctcccggtt cgcgttcccg tcggcggaga | 660 |
| gcgggtcctt ctccccttc tactactcct tcgacgccgg cgggatccac ttcatcatgc | 720 |
| tcggcgccta cgccgactac ggcaggtcag gggagcagta cagatggctg agaaggacc | 780 |
| tggcgaaggt ggacaggtcg gtgacccct ggctggtggc cggctggcac gcgccatggt | 840 |
| acgccacgta caaggctcac tacagggagg tggagtgcat gagagtggcc atggaggagc | 900 |
| tgctctactc ccacggcctc gacatcgcct tcaccggcca tgtgcacgcg tacgagcgct | 960 |
| ccaaccgggt gttcaactac acgctggacc cgtgcggcgc cgtgtacatc tcggtgggcg | 1020 |
| acggcgggaa ccgggagaag atggccacca cccacgccga cgagccgggg cactgcccgg | 1080 |
| acccgcggcc aaagcccaac gccttcattg ccggcttctg cgcctttaac ttcacgtccg | 1140 |
| gcccggccgc cggcaggttc tgctgggacc ggcagccgga ctacagcgcg taccgggaga | 1200 |
| gcagcttcgg ccatggcatc ctcgaggtga agaacgagac gcacgctctg tggagatggc | 1260 |
| acaggaacca ggacctgtac gggagcgccg gagatgagat ttacattgtt cgggagccgg | 1320 |
| aaaggtgctg gcacaagcac aactggacca ggcccgcaca cggtccgtaa | 1370 |

<210> SEQ ID NO 11
<211> LENGTH: 1220
<212> TYPE: DNA
<213> ORGANISM: Hordeum vulgare

<400> SEQUENCE: 11

| | |
|---|---|
| atgtcgattt ggaggggggtc gctgccgctg tttctgcttc tgctcgcggc ggcgacggct | 60 |
| gagccggcgt cgatgctgga gggcccgtct gggccggtga cggtgctgct gcaggaagac | 120 |
| aggggccacg cggtggacct gccggacacg gaccccgggg tgcagcgccg ggtcacaggc | 180 |
| tgggctcccg agcagatcgc cgtcgcgctc tccgccgctc ccacctccgc ctgggtctca | 240 |
| tggatcacag gggatttcca gatgggcggc gctgtcaagc cgctggaccc aggcacggtc | 300 |
| ggcagcgtcg tgcgctacgg cctcgccgcc gattctgtgg tccgcgaggc caccggcgac | 360 |
| gcgctcgtct acagccagct ctacccctt gagggcctcc agaactacac ctccggcatc | 420 |
| atccaccacg tccgcctcca aggtcttgag cctgggacga agtactacta ccagtgcggc | 480 |
| gacccggcca tccgggggc gatgagcgcc gtccacgcat tccggacgat gccggccgtg | 540 |
| gggccgcgga gctacccggg gaggatcgcc gtggtgggag atctcgggct cacgtacaac | 600 |
| accacgtcga ccgtggagca catggcgagc aaccagccgg acctggtcct cctggtcggc | 660 |
| gacgtgagct acgccaacct gtacctgacc aacggcacgg aacagactg ctactcctgc | 720 |
| tcgttcgcca agtccacgcc catccacgag acgtaccagc cgcgctggga ttactgggga | 780 |
| aggtacatgg agcccgtgac gtcgagcacg ccgatgatgt tggtcgaagg gaaccacgag | 840 |
| atcgagcagc agatcggcaa caagaccttc gcggcttaca gcgcgcggtt cgcgttcccg | 900 |
| tcgaaagaga gcgagtcctt ctcccccttc tactactcct tcgacgttgg cggcatccat | 960 |
| ttcatcatgc tcgctgccta cgcgaactac agtaaatcag gagaccagta cagatggttg | 1020 |
| gagaaggacc tagcaaaggt ggatagatca gtgaccccat ggctggtcgc cgggtggcac | 1080 |
| gcgccgtggt acagcaccta caaggctcac tacagggagg cggagtgcat gagagtggcc | 1140 |
| atggaggagc tgctctactc ctacggcatc gacatcgtct tcaccggcca tgtgcacgcg | 1200 |
| tacgagcgct ccaaccgggt | 1220 |

<210> SEQ ID NO 12
<211> LENGTH: 406

```
<212> TYPE: PRT
<213> ORGANISM: Hordeum vulgare

<400> SEQUENCE: 12

Met Ser Ile Trp Arg Gly Ser Leu Pro Leu Phe Leu Leu Leu Leu Ala
1               5                   10                  15

Ala Ala Thr Ala Glu Pro Ala Ser Met Leu Glu Gly Pro Ser Gly Pro
            20                  25                  30

Val Thr Val Leu Leu Gln Glu Asp Arg Gly His Ala Val Asp Leu Pro
        35                  40                  45

Asp Thr Asp Pro Arg Val Gln Arg Arg Val Thr Gly Trp Ala Pro Glu
    50                  55                  60

Gln Ile Ala Val Ala Leu Ser Ala Ala Pro Thr Ser Ala Trp Val Ser
65                  70                  75                  80

Trp Ile Thr Gly Asp Phe Gln Met Gly Gly Ala Val Lys Pro Leu Asp
                85                  90                  95

Pro Gly Thr Val Gly Ser Val Val Arg Tyr Gly Leu Ala Ala Asp Ser
            100                 105                 110

Val Val Arg Glu Ala Thr Gly Asp Ala Leu Val Tyr Ser Gln Leu Tyr
        115                 120                 125

Pro Phe Glu Gly Leu Gln Asn Tyr Thr Ser Gly Ile Ile His His Val
    130                 135                 140

Arg Leu Gln Gly Leu Glu Pro Gly Thr Lys Tyr Tyr Tyr Gln Cys Gly
145                 150                 155                 160

Asp Pro Ala Ile Pro Gly Ala Met Ser Ala Val His Ala Phe Arg Thr
                165                 170                 175

Met Pro Ala Val Gly Pro Arg Ser Tyr Pro Gly Arg Ile Ala Val Val
            180                 185                 190

Gly Asp Leu Gly Leu Thr Tyr Asn Thr Thr Ser Thr Val Glu His Met
        195                 200                 205

Ala Ser Asn Gln Pro Asp Leu Val Leu Leu Val Gly Asp Val Ser Tyr
    210                 215                 220

Ala Asn Leu Tyr Leu Thr Asn Gly Thr Gly Thr Asp Cys Tyr Ser Cys
225                 230                 235                 240

Ser Phe Ala Lys Ser Thr Pro Ile His Glu Thr Tyr Gln Pro Arg Trp
                245                 250                 255

Asp Tyr Trp Gly Arg Tyr Met Glu Pro Val Thr Ser Ser Thr Pro Met
            260                 265                 270

Met Val Val Glu Gly Asn His Glu Ile Glu Gln Gln Ile Gly Asn Lys
        275                 280                 285

Thr Phe Ala Ala Tyr Ser Ala Arg Phe Ala Phe Pro Ser Lys Glu Ser
    290                 295                 300

Glu Ser Phe Ser Pro Phe Tyr Tyr Ser Phe Asp Val Gly Gly Ile His
305                 310                 315                 320

Phe Ile Met Leu Ala Ala Tyr Ala Asn Tyr Ser Lys Ser Gly Asp Gln
                325                 330                 335

Tyr Arg Trp Leu Glu Lys Asp Leu Ala Lys Val Asp Arg Ser Val Thr
            340                 345                 350

Pro Trp Leu Val Ala Gly Trp His Ala Pro Trp Tyr Ser Thr Tyr Lys
        355                 360                 365

Ala His Tyr Arg Glu Ala Glu Cys Met Arg Val Ala Met Glu Glu Leu
    370                 375                 380
```

-continued

```
Leu Tyr Ser Tyr Gly Ile Asp Ile Val Phe Thr Gly His Val His Ala
385                 390             395                 400

Tyr Glu Arg Ser Asn Arg
                405
```